(12) United States Patent
Wacnik et al.

(10) Patent No.: US 8,843,209 B2
(45) Date of Patent: Sep. 23, 2014

(54) RAMPING PARAMETER VALUES FOR ELECTRICAL STIMULATION THERAPY

(75) Inventors: Paul W. Wacnik, Pittsburgh, PA (US); Lisa M. Johanek, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 104 days.

(21) Appl. No.: 13/458,389

(22) Filed: Apr. 27, 2012

(65) Prior Publication Data

US 2013/0289667 A1    Oct. 31, 2013

(51) Int. Cl.
*A61N 1/00*    (2006.01)

(52) U.S. Cl.
USPC .................................. 607/72; 607/2

(58) Field of Classification Search
USPC ........................ 607/6, 39–41, 72, 2
See application file for complete search history.

(56) References Cited

U.S. PATENT DOCUMENTS

| | | | |
|---|---|---|---|
| 6,895,280 B2 | 5/2005 | Meadows et al. | |
| 7,330,762 B2 | 2/2008 | Boveja et al. | |
| 7,463,927 B1 | 12/2008 | Chaouat | |
| 7,634,317 B2 | 12/2009 | Ben-David et al. | |
| 7,738,963 B2 | 6/2010 | Hickman et al. | |
| 8,060,208 B2 | 11/2011 | Kilgore et al. | |
| 2001/0007949 A1 | 7/2001 | Silverstone | |
| 2008/0058901 A1* | 3/2008 | Ternes et al. | 607/59 |
| 2009/0024186 A1 | 1/2009 | Brockway et al. | |
| 2009/0270947 A1* | 10/2009 | Stone et al. | 607/59 |
| 2010/0280500 A1* | 11/2010 | Skelton et al. | 604/891.1 |
| 2011/0022114 A1 | 1/2011 | Navarro | |
| 2011/0208271 A1 | 8/2011 | Dobak | |
| 2011/0307027 A1* | 12/2011 | Sharma et al. | 607/40 |
| 2012/0053660 A1* | 3/2012 | Dobak, III | 607/72 |
| 2013/0204156 A1* | 8/2013 | Hampton et al. | 600/546 |

FOREIGN PATENT DOCUMENTS

| | | |
|---|---|---|
| EP | 1575664 B1 | 2/2010 |
| WO | 2007087332 A3 | 8/2007 |
| WO | 2010051411 A1 | 5/2010 |
| WO | 2010051424 A1 | 5/2010 |
| WO | 2010051425 A2 | 5/2010 |
| WO | 2010059839 A2 | 5/2010 |
| WO | 2010088533 A1 | 8/2010 |

OTHER PUBLICATIONS

Pantaleao et al., "An Investigation of the Effect of Adjusting Pulse Amplitude During TENS Application," Presentation No. PW 480, Presentation Date Sep. 1, 2010, 2 pgs., http://www.abstractsonline.com.

(Continued)

*Primary Examiner* — Catherine Voorhees
(74) *Attorney, Agent, or Firm* — Shumaker & Sieffert, P.A.

(57) ABSTRACT

Devices, systems, and techniques for ramping one or more parameter values of electrical stimulation are disclosed. An implantable medical device may increase or decrease a parameter value, e.g., amplitude or pulse width, over time to reach a target value of the parameter. In one example, a memory may be configured to store a plurality of amplitude ramp schedules. At least one processor may be configured to obtain a stimulation parameter set that at least partially defines an electrical stimulation therapy, select one of the plurality of amplitude ramp schedules based on a signal frequency of the stimulation parameter set, and increase an amplitude of the electrical stimulation therapy during a ramp period defined by the selected amplitude ramp schedule.

23 Claims, 15 Drawing Sheets

(56) References Cited

OTHER PUBLICATIONS

Kormylo et al., "Assessment of Fiber Types Responsible for Upper Limit of Amplitude in Spinal Cord Stimulation," Presentation No. PH 368, Presentation Date Sep. 2, 2010, 2 pgs., http://www.abstractsonline.com.

Yang et al., "Bipolar Spinal Cord Stimulation Attenuates Mechanical Hypersensitivity at an Intensity that Activates a Small Portion of A-Fiber Afferents in Spinal Nerve-Injured Rats," Neuroscience, 11 pgs., (2011).

* cited by examiner

RAMPING PARAMETER VALUES FOR ELECTRICAL STIMULATION THERAPY

TECHNICAL FIELD

The disclosure relates to electrical stimulation therapy and, more particularly, changing parameter values for electrical stimulation therapy.

BACKGROUND

Electrical stimulators may be external or implanted, and may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. In general, an implantable stimulator delivers neurostimulation therapy in the form of electrical pulses, although other continuous waveforms may also be used. An implantable stimulator may deliver neurostimulation therapy via one or more leads that include electrodes located proximate to target locations associated with the brain, the spinal cord, pelvic nerves, peripheral nerves, or the gastrointestinal tract of a patient. Hence, stimulation may be used in different therapeutic applications, such as deep brain stimulation (DBS), spinal cord stimulation (SCS), pelvic stimulation, gastric stimulation, or peripheral nerve field stimulation (PNFS).

In general, a clinician may select values for a number of programmable parameters in order to define the electrical stimulation therapy to be delivered by the implantable stimulator to a patient. For example, the clinician ordinarily selects one or more electrodes, a polarity of each selected electrode, a voltage or current amplitude, a pulse width, a pulse frequency as stimulation parameters. A group of parameters, such as a group including electrode combination, electrode polarity, current or voltage amplitude, pulse width and pulse rate, may be referred to as a program in the sense that they define the electrical stimulation therapy to be delivered to the patient. The clinician may create one or more programs that each includes a selected group of these stimulation parameters. As the patient receives therapy over time, the patient may select, or the system may automatically select, different programs to change the electrical stimulation. Each program may be directed to treat a different anatomical region of the patient, provide an alternative therapy, and/or otherwise adjust the stimulation therapy.

SUMMARY

In general, the disclosure is directed to devices, systems, and techniques for ramping one or more stimulation parameter values of electrical stimulation. An implantable medical device may increase or decrease a parameter value, e.g., amplitude, pulse frequency, or pulse width, over time to reach a target value of the parameter. Gradually increasing the value of a stimulation parameter, e.g., current or voltage amplitude, may enable a patient to receive higher intensity electrical stimulation therapy than would otherwise be possible. The ramp of the gradual increase may be selected based on a signal frequency (e.g., a pulse frequency or a pulse rate) of the stimulation or iteratively selected to achieve higher intensity electrical stimulation therapy.

In one example, the disclosure is directed to a method for controlling electrical stimulation therapy that includes obtaining, by one or more processors, a stimulation parameter set that at least partially defines an electrical stimulation therapy, selecting, by the one or more processors, an amplitude ramp schedule based on a signal frequency of the stimulation parameter set, and increasing, by the one or more processors, an amplitude of the electrical stimulation therapy during a ramp period defined by the amplitude ramp schedule.

In another example, the disclosure is directed to a device that includes a memory configured to store a plurality of amplitude ramp schedules, and at least one processor configured to obtain a stimulation parameter set that at least partially defines an electrical stimulation therapy, select one of the plurality of amplitude ramp schedules based on a signal frequency of the stimulation parameter set, and increase an amplitude of the electrical stimulation therapy during a ramp period defined by the selected amplitude ramp schedule.

In another example, the disclosure is directed to an implantable medical device that includes a memory configured to store a plurality of amplitude ramp schedules and at least one processor configured to obtain a stimulation parameter set that at least partially defines an electrical stimulation therapy, select one of the plurality of amplitude ramp schedule based on a signal frequency of the stimulation parameter set, and increase an amplitude of the electrical stimulation therapy during a ramp period defined by the selected amplitude ramp schedule.

In a further example, the disclosure is directed to a computer-readable storage medium including instructions that cause at least one processor to obtain a stimulation parameter set that at least partially defines an electrical stimulation therapy, select an amplitude ramp schedule based on a signal frequency of the stimulation parameter set, and increase an amplitude of the electrical stimulation therapy during a ramp period defined by the selected amplitude ramp schedule.

The details of one or more example are set forth in the accompanying drawings and the description below. Other features, objects, and advantages will be apparent from the description and drawings, and from the claims.

DETAILED DESCRIPTION

Figure 1:
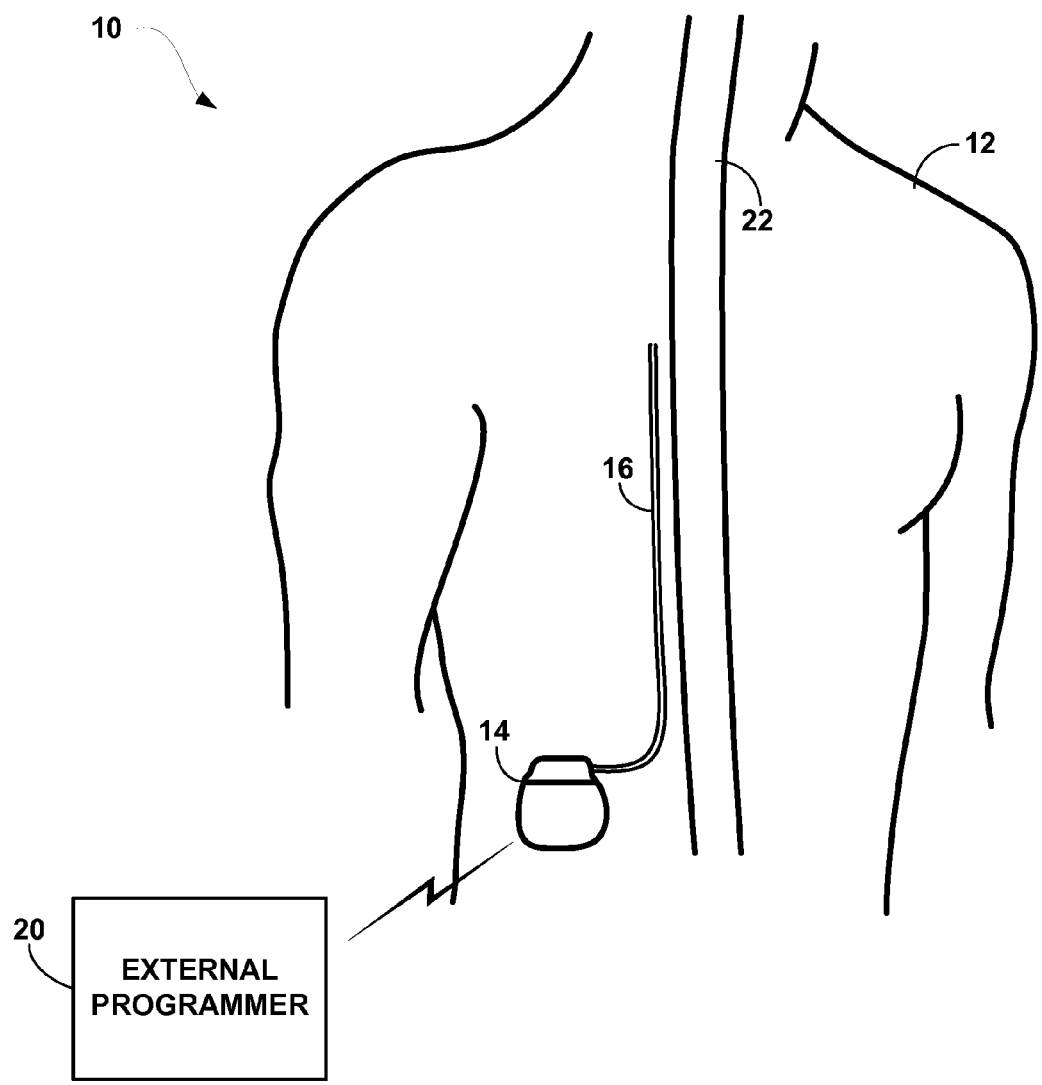
FIG. 1 is a conceptual diagram illustrating an example system that includes an implantable medical device (IMD) for delivering spinal cord stimulation therapy.

This disclosure is generally directed to devices, systems, and techniques for ramping one or more stimulation parameter values of electrical stimulation. Electrical stimulation using higher intensities (e.g., increased voltage amplitude, current amplitude, pulse frequency, and/or pulse width) may provide a greater degree of efficacy to a patient in treating certain symptoms. For example, some patients may benefit from higher intensity electrical stimulation for managing pain. Higher intensity stimulation with increased pulse frequency or increased amplitude may generate stronger paresthesia and/or a greater area of paresthesia. For example, higher pulse frequencies or amplitudes may provide stronger neuronal inhibition than is possible at lower pulse frequencies or amplitudes. In addition, higher intensity stimulation may provide greater long term efficacy.

However, abruptly turning on electrical stimulation or changing one or more stimulation parameters of delivered electrical stimulation may be undesirable to a patient. These relatively fast changes to electrical stimulation may be perceived as pain by the patient and thus be intolerable as therapy. In spinal cord stimulation, high intensity electrical stimulation may be beneficial in treating pain. However, the high intensity stimulation, if delivered too quickly, may result in increased activation or recruitment of A-beta fibers which may feel uncomfortable during a sudden onset. A sudden intensity change may also cause activation of C-delta and A-delta fibers, resulting in uncomfortable stimulation A gradual increase in one or more stimulation parameters may thus allow a patient to receive electrical stimulation without provoking an undesirable physiological response. Furthermore, gradual increases (e.g., ramping) of one or more stimulation parameters may allow the patient to receive electrical stimulation at higher intensities and achieve greater efficacy in treatment than would be tolerable by the patient without such gradual ramping. Although a gradual increase to a stimulation parameter may be beneficial to the patient, the amount of time used to increase the stimulation parameter (e.g., the ramp period) may be balanced by the desire to reach efficacious stimulation intensities quickly.

As disclosed herein, a ramp schedule may be selected to change at least one stimulation parameter gradually such that higher stimulation intensities may be accepted by the patient. In some examples, the ramp schedule may be selected based on the signal frequency (e.g., a pulse frequency or a continuous waveform frequency) of the electrical stimulation. A pulse frequency (e.g., a pulse frequency greater than 250 Hz or greater than 1,000 Hz) higher than typical pulse frequencies (e.g., a pulse frequency less than approximately 250 Hz) may provide increased neuronal inhibition and decreased pain perception in the patient. However, higher pulse frequencies may be less tolerable to the patient. When selecting a ramp schedule for electrical stimulation with a higher pulse frequency, a processor or other device, e.g., an implantable medical device (IMD), may select the ramp schedule to balance a gradual ramp of amplitude, for example, with the desire to reach efficacious amplitude values quickly.

In this manner, an amplitude ramp schedule may be selected based on the pulse frequency of the electrical stimulation. An amplitude ramp schedule may be selected with a longer ramp period and/or a lower rate of amplitude increase for electrical stimulation of higher pulse frequencies. For example, the ramp period for increasing the amplitude of electrical stimulation with a pulse frequency of approximately 1.0 kilohertz (kHz) may be approximately five minutes and the ramp period for increasing the amplitude of electrical stimulation with a pulse frequency of approximately 6.0 kHz may be approximately ten minutes. In an alternative example, the ramp period and/or rate of amplitude increase may be selected to facilitate stimulation delivery at any pulse frequency with a target amplitude. This frequency-dependent ramp schedule may thus allow higher frequency, higher intensity, and more efficacious electrical stimulation to be tolerable by the patient. The relationship between pulse frequencies and ramp schedules (e.g., ramp periods and/or rates of amplitude increase) for changing current or voltage amplitude may be linear, exponential, polynomic, or stepwise. This relationship may also be selected by a clinician, patient specific, or even adaptable based on patient input over time.

In addition, a patient may tolerate electrical stimulation therapy with higher pulse frequencies and/or higher amplitudes if the pulse width is reduced. For example, the pulse width may be selected based on the pulse frequency of the electrical stimulation. A relationship between pulse frequency and pulse width may be used to select an appropriate pulse width for electrical stimulation having greater pulse frequencies. In other examples, a device may ramp down the pulse width as the amplitude is ramped up. Without changing any other stimulation parameters, decreasing the pulse width may reduce the overall intensity of the electrical stimulation and/or reduce the number of nerve fibers affected by the electrical stimulation. When reducing the pulse width at the same time amplitude is increased, the paresthesia sensed by the patient may or may not increase in anatomical area. The ramp schedule of the pulse width may or may not be dependent upon the pulse frequency of the electrical stimulation.

In other examples, an IMD and/or an external programmer may iteratively ramp an amplitude or other stimulation parameter over time to achieve higher stimulation intensities and efficacious stimulation therapy for the patient. Iterative ramping may refer to a gradual process in which a stimulation parameter value is ramped over time to slowly increase the stimulation intensity acceptable to the patient. During iterative ramping, a ramp schedule may be selected such that the ramp period for a continuous ramp is on the order of minutes, hours, or even days. For example, a single continuous ramp period during the iterative ramping process may be between approximately 20 minutes and 8 hours.

In one example, the IMD may start at a minimal amplitude (e.g., zero amplitude or a nonzero amplitude below a perception threshold of the patient) and slowly increase the amplitude during the ramp period. Once the amplitude has reached a maximum tolerable amplitude value for the patient, the programmer and/or IMD may receive a hold input that commands the IMD to stop the amplitude ramping, maintain the electrical stimulation at that amplitude value, and/or store the amplitude value used to define stimulation when the hold input was received. In some examples, the IMD may subsequently begin to ramp the amplitude again from the stored amplitude value to attempt in increase the tolerable stimulation intensity for the patient. In other examples, when the patient returns to the same therapy program of the stored amplitude from the previous ramp period, the IMD may again begin at the minimal amplitude value and ramp the amplitude again in an attempt to increase the amplitude above the previous amplitude value stored for the program. In this manner, iterative ramping may be an effective process to slowly increase the stimulation intensity acceptable to the patient during therapy.

Electrical stimulation, including the various ramping techniques described herein, may be delivered with a continuous waveform or discrete pulses. Electrical stimulation will be generally described herein as being delivered in the form of pulses, such as stimulation defined by pulse frequency, pulse width, and current or voltage amplitude. However, electrical stimulation may alternatively be delivered according to the various techniques herein in the form of a continuous waveform. The continuous waveform may take the form of a sinusoidal waveform, unsymmetrical waveform, or any other shapes. A continuous waveform may also be defined by similar parameters to that of pulse waveforms described herein.

FIG. 1 is a conceptual diagram illustrating an example system 10 that includes an implantable medical device (IMD) 14 for delivering spinal cord stimulation (SCS) therapy. Although the techniques described in this disclosure are generally disclosed with respect to pain management therapy for illustration, other types of therapy may incorporate one or more ramping techniques disclosed herein. In addition, FIG. 1 is directed to SCS therapy. However, system 10 may alternatively be configured to provide peripheral nerve field stimulation (PNFS) of FIG. 2, occipital nerve stimulation, gastric nerve stimulation, sacral nerve stimulation (SNS), pelvic floor stimulation, or any other electrical stimulation therapy.

As shown in FIG. 1, system 10 includes an IMD 14 and external programmer 20 shown in conjunction with a patient 12, who is ordinarily a human patient. In the example of FIG. 1, IMD 14 is an implantable electrical stimulator that delivers neurostimulation therapy to patient 12, e.g., for relief of chronic pain or other symptoms. Generally IMD 14 may be a chronic electrical stimulator that remains implanted within patient 12 for weeks, months, or even years. In the example of FIG. 1, IMD 14 and lead 16 may be directed to delivering SCS therapy. In other examples, IMD 14 may be a temporary, or trial, stimulator used to screen or evaluate the efficacy of electrical stimulation for chronic therapy. IMD 14 may be implanted in a subcutaneous tissue pocket, within one or more layers of muscle, or other internal location. IMD 14 may be coupled to one or more lead 16.

Electrical stimulation energy, which may be constant current or constant voltage based pulses, for example, is delivered from IMD 14 to one or more targeted locations within patient 12 via one or more electrodes (not shown) of lead 16. The parameters for a program that controls delivery of stimulation energy by IMD 14 may include information identifying which electrodes have been selected for delivery of stimulation according to a stimulation program, the polarities of the selected electrodes, i.e., the electrode configuration for the program, and voltage or current amplitude, pulse frequency (or pulse rate), pulse shape, and pulse width of stimulation delivered by the electrodes. Electrical stimulation may be delivered in the form of stimulation pulses or continuous waveforms, for example.

In the example of FIG. 1, lead 16 is disposed within patient 12, e.g., implanted within patient 12. Lead 16 tunnels through tissue of patient 12 from along spinal cord 22 to a subcutaneous tissue pocket or other internal location where IMD 14 is disposed. Although lead 16 may be a single lead, lead 16 may include a lead extension or other segments that may aid in implantation or positioning of lead 16. In addition, a proximal end of lead 16 may include a connector (not shown) that electrically couples to a header of IMD 14. Although only one lead 16 is shown in FIG. 1, system 10 may include two or more leads, each coupled to IMD 14 and directed to similar or different target tissue sites. For example, multiple leads may be disposed along spinal cord 22 or leads may be directed to spinal cord 22 and/or other locations within patient 12.

Lead 16 may carry one or more electrodes that are placed adjacent to the target tissue, e.g., spinal cord 22 for spinal cord stimulation (SCS) therapy. One or more electrodes may be disposed at or adjacent a distal tip of lead 16 and/or at other positions at intermediate points along lead 16, for example. Electrodes of lead 16 transfer electrical stimulation generated by an electrical stimulation generator in IMD 14 to tissue of patient 12. The electrodes may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode configurations for therapy. In general, ring electrodes arranged at different axial positions at the distal ends of lead 16 will be described for purposes of illustration.

In alternative examples, lead 16 may be configured to deliver stimulation energy generated by IMD 14 to stimulate one or more sacral nerves of patient 12, e.g., sacral nerve stimulation (SNS). SNS may be used to treat patients suffering from any number of pelvic floor disorders such as pain, urinary incontinence, fecal incontinence, sexual dysfunction, or other disorders treatable by targeting one or more sacral nerves. Lead 16 and IMD 14 may also be configured to provide other types of electrical stimulation or drug therapy (e.g., with lead 16 configured as a catheter). For example, lead 16 may be configured to provide deep brain stimulation (DBS), peripheral nerve field stimulation (PNFS), gastric nerve stimulation, or other deep tissue or superficial types of electrical stimulation. In other examples, lead 16 may provide one or more sensors configured to allow IMD 14 to monitor one or more parameters of patient 12. The one or more sensors may be provided in addition to, or in place of, therapy delivery by lead 16.

IMD 14 delivers electrical stimulation therapy to patient 12 via selected combinations of electrodes carried by lead 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue for electrical stimulation delivered via lead 16 is tissue proximate spinal cord 22 (e.g., one or more target locations of the dorsal columns or one or more dorsal roots that branch from spinal cord 22). Lead 16 may be introduced into spinal cord 22 via any suitable region, such as the thoracic, cervical or lumbar regions. Stimulation of dorsal columns, dorsal roots, and/or peripheral nerves (e.g., afferent nerves) may, for example, prevent pain signals from traveling through spinal cord 22 and to the brain of the patient. Patient 12 may perceive the interruption of pain signals as a reduction in pain and, therefore, efficacious therapy results. For treatment of other disorders, lead 16 may be introduced to other internal locations from an implanted device or from an external device using a percutaneous lead.

Although lead 16 is described as generally delivering or transmitting electrical stimulation signals, lead 16 may additionally transmit electrical signals from patient 12 to IMD 14 for monitoring. For example, IMD 14 may utilize detected nerve impulses to diagnose the condition of patient 12 or adjust the delivered stimulation therapy. Lead 16 may thus transmit electrical signals to and from patient 12.

A user, such as a clinician or patient 12, may interact with a user interface of an external programmer 20 to program IMD 14. Programming of IMD 14 may refer generally to the generation and transfer of commands, programs, or other information to control the operation of IMD 14. In this manner, IMD 14 may receive the transferred commands and programs from programmer 20 to control stimulation therapy. For example, external programmer 20 may transmit programs, parameter adjustments, program selections, group selections, user input, or other information to control the operation of IMD 14, e.g., by wireless telemetry or wired connection.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer may be generally accessible to patient 12 and, in many cases, may be a portable device that may accompany patient 12 throughout the patient's daily routine. For example, a patient programmer may receive input from patient 12 when the patient wishes to hold a ramping amplitude or terminate or change stimulation therapy when the stimulation is undesirable. In general, a physician or clinician programmer may support selection and generation of programs by a clinician for use by stimulator 14, whereas a patient programmer may support adjustment and selection of such programs by a patient during ordinary use. In other examples, external programmer 20 may be included, or part of, an external charging device that recharges a power source of IMD 14. In this manner, a user may program and charge IMD 14 using one device, or multiple devices.

IMD 14 may be constructed of any polymer, metal, or composite material sufficient to house the components of IMD 14 (e.g., components illustrated in FIG. 2) within patient 12. In this example, IMD 14 may be constructed with a biocompatible housing, such as titanium or stainless steel, or a polymeric material such as silicone or polyurethane, and surgically implanted at a site in patient 12 near the pelvis, abdomen, or buttocks. The housing of IMD 14 may be configured to provide a hermetic seal for components, such as rechargeable power source 18. In addition, the housing of IMD 14 may be selected of a material that facilitates receiving energy to charge rechargeable power source 18.

As described herein, information may be transmitted between external programmer 20 and IMD 14. Therefore, IMD 14 and programmer 20 may communicate via wireless communication using any techniques known in the art. Examples of communication techniques may include, for example, radiofrequency (RF) telemetry, but other techniques are also contemplated. In some examples, programmer 20 may include a communication head that may be placed proximate to the patient's body near the implant site of IMD 14. This close proximity of programmer 20 to IMD 14 may improve the quality or security of communication between IMD 14 and programmer 20. Communication between programmer 20 and IMD 14 may occur during power transmission or separate from power transmission.

As further described herein, IMD 14 and/or programmer 20 may increase or decrease (e.g., ramp) a stimulation parameter value to achieve desirable electrical stimulation therapy. In one example, one or more processors (of IMD 14 and/or programmer 20) may obtain a stimulation parameter set that at least partially defines an electrical stimulation therapy, select an amplitude ramp schedule based on a pulse frequency of the stimulation parameter set, and increase an amplitude of the electrical stimulation therapy during a ramp period defined by the amplitude ramp schedule. In this manner, specifications for how IMD 14 may ramp up or ramp down an amplitude value may be determined as a function of the pulse frequency. Since the pulse frequency may at least partially determine the perceived intensity of the electrical stimulation or the degree to which the electrical stimulation is tolerable when treating the patient condition, the ramp schedule may be selected to match or correspond to the pulse frequency with which the electrical stimulation will be delivered.

In addition, IMD 14 may house or otherwise include a therapy module configured to generate and deliver electrical stimulation to patient 14 when increasing the amplitude of the electrical stimulation during the ramp period. The therapy module may include a stimulation generator and any circuits necessary to generate electrical stimulation pulses or waveforms according to the parameter values of the stimulation parameter set. Accordingly, the therapy module may generate stimulation pulses according to the stimulation parameters selected by one or more processors. The generated stimulation may be delivered via lead 16 to patient 16.

A ramp schedule may at least partially define how IMD 14 increases or decreases a parameter value over time. For example, the ramp schedule may define a rate of increasing a parameter value (e.g., an amplitude value). In addition, or alternatively, the ramp schedule may define a ramp period during which the parameter (e.g., the amplitude) is increased. IMD 14 and/or programmer 20 may generate a starting value and intermediate values for the parameter to be increased based on the target parameter value, the rate of increase, and/or the ramp period. Alternatively, the ramp schedule may include the starting value and, in some examples, the intermediate values to be used when increasing the parameter value during the ramp period. Although a ramp schedule may be selected for increasing a parameter value during the ramp period, a ramp schedule may alternatively be selected for decreasing the parameter value during the ramp period. In this manner, a parameter value may be ramped "up" or "down" in various circumstances. IMD 14 and/or programmer 20 may also include a memory configured to store a plurality of ramp schedules (e.g., a table of ramp schedules or one or more equations from which a ramp schedule may be selected). A ramp schedule may thus be retrieved from the memory based on the pulse frequency of a stimulation parameter set, for example.

The ramp schedule may be selected by a processor of IMD 14 or programmer 20 based on the pulse frequency of the stimulation parameter set. In other words, different ramp schedules may be selected for different pulse frequency values. In one example, a ramp period for increasing the amplitude of the electrical stimulation may be longer for higher pulse frequencies than lower pulse frequencies. In other words, electrical stimulation defined by higher pulse frequencies, or more frequent pulses, may require a longer ramp period for increasing the amplitude to the target amplitude than electrical stimulation defined by lower pulse frequencies.

In another example, the ramp schedule may define a rate of increasing a parameter, such as amplitude. The rate of increasing the amplitude value during the ramp may be lower for higher pulse frequencies than lower pulse frequencies. In other words, IMD 14 may more slowly, or more gradually, increase the amplitude of the electrical stimulation when the pulse frequency is higher. More gradual amplitude increases may allow patient 12 to tolerate electrical stimulation with more frequent pulses. Although IMD 14 may generally ramp amplitude based on the pulse frequency, IMD 14 may ramp one or more other parameter values according to the pulse frequency of the electrical stimulation.

In other examples, a ramp schedule may be selected for ramping (e.g., increasing or decreasing) a pulse width of the electrical stimulation. In one example, the pulse width may be decreased according to a pulse width ramp schedule concurrently with ramping up the amplitude. IMD 14 or programmer 20 may select the pulse width ramp schedule based on the selected amplitude ramp schedule. The pulse width ramp schedule may be selected such that the ramp period of the pulse width is equal to the ramp period of the amplitude. IMD 14 may then decrease the pulse width of the electrical stimulation therapy while IMD 14 increases the amplitude during the ramp period.

Concurrent ramping of two stimulation parameters may generally refer to the ramp periods for each of the stimulation parameters, where the ramp periods are entirely or at least partially overlapping with one another. In some examples, the two ramp periods may entirely overlap or even be executed during the same and equal duration. Concurrent ramping may refer to both of the ramped parameters changing for the same pulse. In other words, the amplitude may increase and the pulse width may decrease for the same pulse when compared to the previous pulse. Alternatively, a subsequent pulse may only include a single parameter value change when compared to the previous pulse. In other words, the amplitude ramp up and the pulse width ramp down may be interleaved between pulses. As an illustration, amplitude and pulse width could be gradually increased on an alternating basis among pulses, or bursts of pulses, such that one of amplitude and pulse width is increased or decreased for a first pulse or burst, then the other is increased or decreased for a second pulse or burst, and then the process repeats on an alternating basis over a series of pulses or bursts of pulses. In addition, ramping a stimulation parameter may not require each subsequent pulse to have a different parameter value than the previous pulse. Instead, consecutive pulses may still be defined by identical parameter values in some examples.

In some examples, the pulse width ramp schedule may be based on a pulse frequency. In other examples, the pulse width ramp schedule may be selected based on an amplitude ramp schedule or independent of any electrical stimulation parameters. Increasing or decreasing pulse width values may allow IMD 14 and/or programmer 20 to control the extent to which paresthesia is perceived by patient 14. Longer pulse widths may increase the number of nerve fibers recruited during the pulse. Therefore, decreasing the pulse width may decrease the number of nerve fibers affected by the electrical stimulation and decrease the anatomical area in which patient 12 perceives the electrical stimulation.

Increasing or decreasing the pulse width of electrical stimulation may also be used to control the extent to which paresthesia is perceived by patient 14. As amplitude is increased during a ramp period, for example, the increased amplitude, and stimulation intensity, may result in an increased area of paresthesia. The increased amplitude may also increase the extent of neuronal inhibition on affected nerves. Although patient 14 may desire the increased inhibition from greater stimulation amplitudes, the increased paresthesia area may not be desirable. Therefore, as amplitude is increased during the ramp period, the pulse width of stimulation may be correspondingly decreased. The resulting therapeutic effect on patient 14 may be a perceived increase in inhibition in pain signals transmitted to the affected nerves while limiting the area to which paresthesia is perceived by patient 14.

IMD 14 may obtain a stimulation parameter set and select a ramp schedule for decreasing or increasing pulse width based on at least one of the parameter values of the stimulation parameter set. In some examples, the pulse width ramp schedule may be at least partially based on an amplitude of the parameter set and/or an amplitude ramp schedule. IMD 14 may thus increase or decrease the pulse width during a ramp period as defined by the selected ramp schedule and deliver the corresponding electrical stimulation to patient 14. When IMD 14 ramps the pulse width inversely to the amplitude, each ramp schedule and/or parameter values may be selected to maintain a relatively consistent paresthesia area for patient 14.

The stimulation parameter set may include respective values for an electrode configuration, a current amplitude, a voltage amplitude, a pulse frequency, a pulse width, or additional parameters. The stimulation parameter set may include values of the target or desired parameter values (e.g., a target amplitude). In other words, the stimulation parameter set may include parameter values that would at least partially define stimulation therapy after any ramping of one or more values is complete. For example, the amplitude value of the stimulation parameter set may be 4.0 volts, for the example of voltage-based amplitude control. Although IMD 14 may begin to ramp the electrical stimulation at an amplitude of zero volts, for example, the 4.0 volt amplitude value may be the target or desired amplitude of the stimulation parameter set that defines the electrical stimulation. In examples in which current amplitude is controlled (e.g., constant voltage stimulation systems), IMD 14 may have similarly zero current amplitude starting values and nonzero target or desired current amplitudes.

In addition, some stimulation parameter sets may include minimal values and target values for a parameter that will be ramped, or changed, when delivering the electrical stimulation. For example, the stimulation parameter set may include a minimal amplitude value (e.g., 1.0 volts) and a target amplitude value (e.g., 6.0 volts). In this manner, the stimulation parameter set may define the starting and target end points for ramping the parameter value. In other examples, a ramping schedule may include the starting value based on the target value of the parameter stored in the stimulation parameter set.

In some examples, the stimulation parameter set may include a starting amplitude for beginning the ramp period. This starting amplitude may be lower than the target amplitude when increasing the amplitude and higher than the target amplitude when decreasing the amplitude during the ramp period. When the stimulation parameter set includes both a starting amplitude value and a target amplitude value, the selected ramping schedule may define the rate of increasing the amplitude from the starting amplitude to the target amplitude. For example, the rate may be specified as volts or milliamps per minute. Alternatively, the ramp schedule may define a ramp period for arriving at the target amplitude from the starting amplitude. IMD 14 or programmer 20 may thus calculate the appropriate rate of increase based on the defined ramp period.

As described above, the amplitude ramp schedule may be selected based on the pulse frequency of the desired electrical stimulation therapy. In some examples, the pulse frequency may be less than 250 Hz. In other examples, the pulse frequency may be greater than 250 Hz. For example, the pulse frequency may be between approximately 250 Hz and 1,000 Hz. In another example, the pulse frequency may be between approximately 1,000 Hz and 10,000 Hz. Alternatively, the pulse frequency may be greater than 10,000 Hz. These higher pulse frequencies above 1,000 Hz may be greater than the firing potential of the nerves. In any example, amplitude may be ramped up for any pulse frequency that may be perceived as uncomfortable to the patient. The ramp period at least partially defined by the ramp schedule may be between approximately one minute and 90 minutes. In some example, the ramp period may be between approximately 3 minutes and 20 minutes. In other examples, the ramp period may be greater than approximately 90 minutes.

The relationship between the pulse frequency and the selected ramp period may vary based on the type of stimulation, the electrode combination, the location of the electrodes, and patient specific variables. In one example, the relationship between pulse frequency and the ramp period may be a linear relationship. In other examples, the relationship may be described as exponential, polynomial, or even step-wise. Programmer 20 may receive input from a clinician or patient selecting or setting the relationship between the pulse frequency and ramp period and/or rate of parameter value change. Programmer 20 and/or IMD 14 may alternatively modify the relationship between pulse frequency and ramp period or rate of parameter value change based on patient input. For example, if patient 30 is maintaining the amplitude value or terminating stimulation during the ramp period prior to achieving the target amplitude, IMD 14 or programmer 20 may increase the ramp period and/or reduce the rate of amplitude change for that particular frequency and/or a band of frequencies. In other words, the relationship between pulse frequency and ramp period may be adjusted for a single pulse frequency, a band of pulse frequencies, or even the entire relationship curve may be modified.

As described herein, the one or more processors to select ramp schedules and increase or decrease the parameter values may be attributed to IMD 14, programmer 20, and/or another device. For example, the one or more processors may be housed within at least one of IMD 14 and external programmer 20. In some cases, processing functionality may be shared between IMD 14 and external programmer 20, such that IMD 14 and external programmer 20 perform different processing sub-tasks. In another example, IMD 14 may include a memory that stores a plurality of ramp schedules and at least one processor.

In other examples, a system may include one or more components for decreasing a pulse width of electrical stimulation during a ramp period. IMD 14 and/or programmer 20 may include a memory configured to store a plurality of pulse width ramp schedules. IMD 14 and/or programmer 20 may also include at least one processor configured to obtain a stimulation parameter set that at least partially defines an electrical stimulation therapy, select one of the plurality of pulse width ramp schedules based on at least one parameter value of the stimulation parameter set, and change the pulse width of the electrical stimulation therapy during a ramp period defined by the selected pulse width ramp schedule. In some examples, IMD 14 and/or programmer 20 may select an amplitude ramp schedule and change the amplitude concurrently with the pulse width during the ramp period. IMD 14 may increase the amplitude as the pulse width is decreased to control the anatomical area in which patient 14 perceives the electrical stimulation therapy.

In another example, IMD 14 and/or programmer 20 may control the ramping of one or more stimulation parameter values to achieve higher therapeutic stimulation intensities that would otherwise not be tolerable without the ramping of the stimulation parameter values. For example, at least one processor of IMD 14 and/or programmer 20 may obtain a stimulation parameter set that at least partially defines electrical stimulation therapy. The at least one processor may then select a ramp schedule that at least partially defines a ramp period for increasing a stimulation parameter value. Generally, amplitude may be increased during the ramp period. However, pulse width, pulse frequency, or any other stimulation parameter may be selected to be ramped such that the stimulation intensity increases.

The ramp period may be selected such that the target amplitude is greater than known tolerable amplitude values for patient 12. In response to receiving a hold input from patient 12 or programmer 20 that indicates amplitude ramping is to stop, IMD 14 may hold electrical stimulation at the held amplitude value. In one example, IMD 14 may subsequently resume increasing the amplitude in another iteration of the ramping process. In response to receiving another hold input, programmer 20 and/or IMD 14 may again hold the amplitude at the value when the hold input was received. IMD 14 and/or programmer 20 may store the maximum amplitude correlating with the hold inputs received by the user.

In another example, IMD 14 may present subsequent iterations of the ramp period when therapy returns to a previously used therapy program. In other words, subsequent iterations of the ramping process may be employed after IMD 14 delivers therapy with a different therapy program or temporarily terminates stimulation therapy. When IMD 14 subsequently uses a therapy program in which the amplitude has ramped up previously, IMD 14 and/or programmer 20 may control the amplitude to be ramped up from a minimal value (e.g., zero volts or a perception threshold) back to the previous maximum amplitude associated with the latest hold input. This initial ramp period may be shorter than the previously used ramp period (or the rate of increase greater than previously used) to more quickly arrive at the known acceptable amplitude value. In response to reaching the previous stored maximum amplitude, IMD 14 and/or programmer 20 may reduce the rate of increase and/or increase the ramp period to more gradually push the tolerable amplitude value higher than previously achieved amplitudes. Using any of these iterative ramping processes, gradual ramping of amplitude or other stimulation parameters may allow IMD 14 to deliver stimulation therapy with higher intensities than would otherwise be tolerable by patient 14.

For any of the gradual ramping of an iterative ramping process, the ramp periods (e.g., periods in which amplitude is continually increased or decreased) may be relatively long to allow patient 12 to acclimate to the increasing amplitudes. The ramp periods used in the iterative ramping process may be on the order of minutes, hours, or even days. In one example, a ramp period may be between approximately 20 minutes and 8 hours. In another example, the ramp period may be between 30 minutes and 90 minutes. However, the ramp period may also be greater than 8 hours or even greater than 24 hours. The ramp periods may be selected by a clinician, based on patient specific data, and/or adjusted over time as patient receives stimulation therapy.

Although IMD 14 is generally described herein, techniques of this disclosure may also be applicable to external or partially external medical device in other examples. For example, IMD 14 may instead be configured as an external medical device coupled to one or more percutaneous medical leads. The external medical device may be a chronic, temporary, or trial electrical stimulator. In addition, an external electrical stimulator may be used in addition to one or more IMDs 14 to deliver electrical stimulation described herein.

Figure 2:
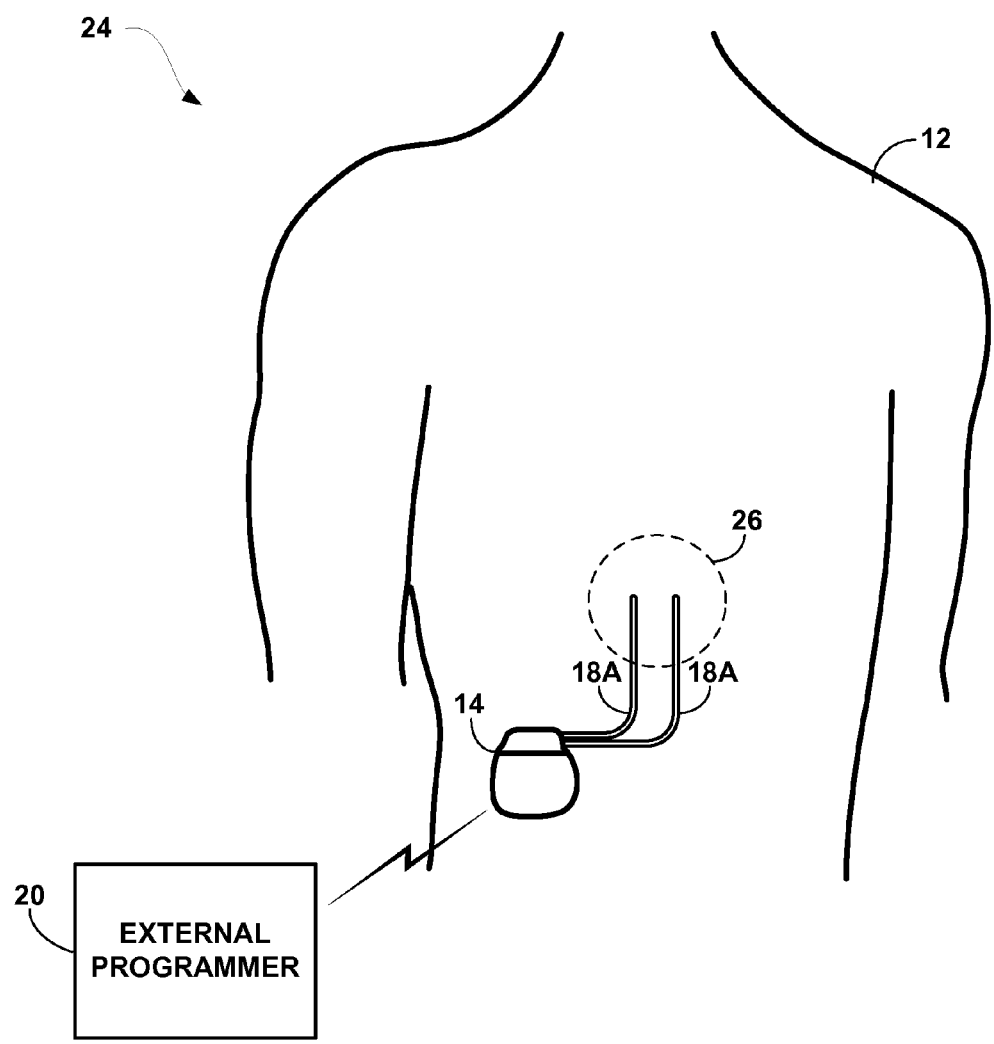
FIG. 2 is a conceptual diagram illustrating an example system that includes an implantable medical device (IMD) for delivering peripheral nerve stimulation therapy.

FIG. 2 is a conceptual diagram illustrating an example system 24 that includes IMD 14 for delivering peripheral nerve field stimulation (PNFS) therapy. IMD 14 may be configured to deliver PNFS therapy using any of the ramping techniques described herein. PNFS may be delivered by a medical device via electrodes implanted in the region (e.g., region 26) where the patient experiences pain. Some examples of programming techniques described herein allow a user, such as a clinician or patient, to determine a therapy program for the PNFS based on user input that specifies one or more characteristics of the stimulation field that is delivered to the region in which the patient experiences pain. The characteristics of the stimulation field may include, for example, a direction of stimulation within the field, a breadth of the stimulation field, a focus of stimulation within the stimulation field, a fiber diameter selectivity, and a depth of the stimulation field relative to a reference point, such as the epidermis of the patient.

As described with respect to FIG. 1, adjusting the amplitude (current or voltage) or pulse width may modify the intensity and/or area of which patient 12 perceives paresthesia during delivery of electrical stimulation. A stimulation parameter set may be selected such that electrical stimulation reduces or eliminates the pain perceived by patient 12 within region 20. In other examples, IMD 14 may be configured to deliver electrical stimulation to multiple separate regions of patient 12.

The stimulation parameter set may include an electrode combination using one or more electrodes of one or both leads 18A and 18B. Each of leads 18A and 18B may be similar to lead 16 of FIG. 1. Electrode combinations used to provide PNFS therapy may be unipolar (e.g., one or more cathodes are provided by lead 18A or 18B and an anode is provided on the housing of IMD 14) or bipolar (e.g., both cathodes and anodes are provided on leads 18A and/or 18B). In other examples, IMD 14 may be coupled to a single lead or more than two leads. Similar to FIG. 1, external programmer 20 may communicate with and transmit parameter sets or other commands to IMD 14.

Some example systems may include more than one IMD 14 for delivery of PNFS to one or more regions in which patient 11 experiences pain. In other examples, PNFS may be delivered alone, or in combination with other therapies, such as spinal cord stimulation (SCS), deep brain stimulation (DBS), cortical stimulation (CS), drug therapy, and the like, as described in U.S. Patent Publication No. 2007/0073356 to Rooney et al., entitled, "COMBINATION THERAPY INCLUDING PERIPHERAL NERVE FIELD STIMULATION," which was filed on Jun. 9, 2006, and is incorporated herein by reference in its entirety.

In the example shown in FIG. 2, leads 18A and 18B deliver PNFS to the tissue of patient 12 within a region 26 where patient 12 experiences pain. Leads 18A and/or 18B may be implanted within or between, for example, intra-dermal, deep dermal, or subcutaneous tissues of patient 12 at the region 26 where patient 12 experiences pain to deliver PNFS. These tissues may include skin and associated nerves and muscles and associated nerves or muscle fibers. In the illustrated example, region 26 is an axial region of the lower back of patient 12, but the disclosure is not limited as such. Rather, leads 18A and 18B may be implanted in any region where patient 12 experiences pain. Leads 18A and/or 18B may deliver PNFS to one layer of tissue or multiple layers of a tissue as determined necessary by a clinician.

PNFS may ameliorate pain within the region of implantation by stimulating axons or small nerve fibers in the nearby dermal, subcutaneous, or muscular tissues, or the tissues themselves. The stimulation of these axons or fibers may cause orthodromic action potentials that propagate toward a spinal cord of patient 12, and modulate larger peripheral nerves (e.g., afferent nerves) and dorsal horn cells and/or synapses within the dermatomes that include the pain region, which may reduce pain experienced by patient 12 in that region. The stimulation of these axons or fibers may also cause antidromic action potentials that propagate toward the skin and modulate sympathetic outflow, which may reduce pain mediated by the sympathetic system, such as with some forms of complex regional pain syndrome.

Like lead 16, lead 18A or 18B may comprise, as examples, a substantially cylindrical lead with ring electrodes, a paddle lead, or a lead with a more complex, three-dimensional electrode array geometry, such as a cylindrical lead with electrodes disposed at various circumferential positions around the cylinder (e.g., with the aid of partial ring electrodes or segmented electrodes disposed at various circumferential positions around a lead having a generally round cross-section). In some examples, leads 18A or 18B may include electrodes, such as pad electrodes or segmented electrodes, on more than one surface. For example, leads 18A and 18B may be a paddle-type lead with electrodes on multiple surfaces, or a multiple level lead, as will be described in greater detail below. In general, the disclosure may be used with a system 10 including any type of lead, and is not limited to the leads described herein, or any particular type of implantable lead.

Figure 3:
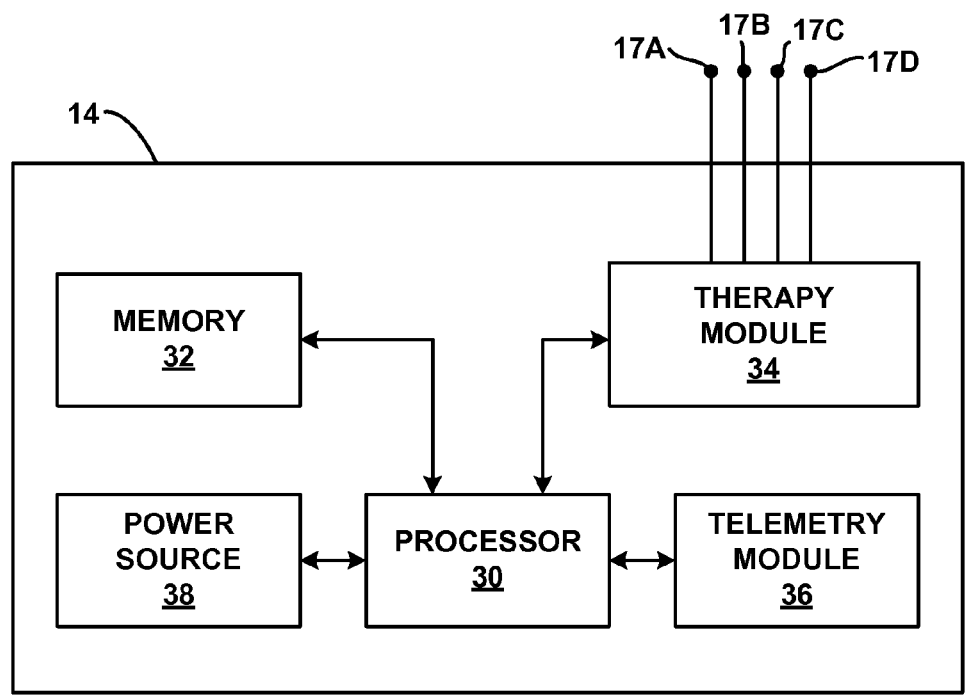
FIG. 3 is a block diagram of the example IMD of FIGS. 1 and 2.

FIG. 3 is a block diagram of the example IMD 14 of FIGS. 1 and 2. In the example of FIG. 3, IMD 14 includes processor 30, therapy module 34, power source 38, memory 32, and telemetry module 36. In other examples, IMD 14 may include a greater or fewer number of components. For example, IMD 14 may also include a temperature sensor, an inductive coil to receive power from an external charging device, and a recharge module that manages recharging of power source 38.

In general, IMD 14 may comprise any suitable arrangement of hardware, alone or in combination with software and/or firmware, to perform the various techniques described herein attributed to IMD 14 and processor 30. In various examples, IMD 14 may include one or more processors 30, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 also, in various examples, may include a memory 32, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processor 30, therapy module 34, and telemetry module 36 are described as separate modules, in some examples, processor 30, therapy module 34, and telemetry module 36 may be functionally integrated. In some examples, processor 30, therapy module 34, and telemetry module 36 may correspond to individual hardware units, such as ASICs, DSPs, FPGAs, or other hardware units.

Memory 32 may store therapy programs or other instructions that specify therapy parameter values for the therapy provided by therapy module 34 and IMD 14. Memory 32 may also store ramp schedules for one or more parameters (e.g., amplitude and pulse width) and any other instructions for ramping a parameter value. In some examples, memory 32 may also store instructions for communication between IMD 14 and programmer 20, or any other instructions required to perform tasks attributed to IMD 14. Memory 32 may store a duplicate of the data stored in memory 52 of programmer 20.

Generally, therapy module 34 may generate and deliver electrical stimulation under the control of processor 30. In some examples, processor 30 controls therapy module 34 by accessing memory 32 to selectively access and load at least one of the stimulation programs to therapy module 34. For example, in operation, processor 30 may access memory 32 to load one of the stimulation programs to therapy module 34. In such examples, relevant stimulation parameters may include a voltage amplitude, a current amplitude, a pulse frequency, a pulse width, a duty cycle, or the combination of electrodes 17A, 17B, 17C, and 17D that therapy module 34 uses to deliver the electrical stimulation signal. In addition, processor 30 may access memory 32 to select an appropriate ramp schedule from a plurality of ramp schedules stored in memory 32. Although therapy module 34 may be configured to generate and deliver electrical stimulation therapy via one or more of electrodes 17A, 17B, 17C, and 17D of lead 16, a different therapy module may be configured to provide different therapy to patient 12, such as drug delivery therapy via a catheter. These and other therapies may be provided by IMD 14.

An exemplary range of electrical stimulation parameters that may be used to deliver effective treatment for chronic pain, e.g., when applied to spinal cord 18, are listed below. While stimulation pulses are described, stimulation signals may be of any of a variety of forms such as sine waves or the like.

Pulse Frequency: between approximately 0.5 Hz and 10,000 Hz. In one example, pulse frequency may be between approximately 5 Hz and 250 Hz or between approximately 30 Hz and 130 Hz. In other examples, pulse frequency may be greater than 250 Hz or even greater than 1,000 Hz. Pulse frequencies greater than 1,000 Hz may be considered to be greater than the nerve firing potential of affected nerve fibers to inhibit nerve firing. For example, the pulse frequency may be between approximately 1,000 Hz and 10,000 Hz. Amplitude values may be ramped up over time based on the pulse frequency selected (e.g., longer ramp periods may be used for higher pulse frequencies).

Amplitude: between approximately 0.1 volts and 50 volts, more preferably between approximately 0.5 volts and 20 volts, and still more preferably between approximately 1 volt and 10 volts. In other examples, a current amplitude may be defined as the biological load in the voltage that is delivered. For example, the range of current amplitude may be between approximately 0.1 milliamps (mA) and 50 mA. In other examples, current amplitude may be between approximately 1.0 mA and 10 mA.

Pulse Width: between about 10 microseconds and 5000 microseconds. In some examples, the pulse width may be between approximately 100 microseconds and 1000 microseconds or between approximately 180 microseconds and 450 microseconds. With higher frequency pulses, the pulse width may be smaller to accommodate the increased frequency. For example, the pulse width may be between approximately 10 microseconds and 50 microseconds.

In addition, pulses used to deliver electrical stimulation may take different shapes. Pulses may be rectangular, square, triangular, trapezoidal, symmetrical, or unsymmetrical. Consecutive pulses may have similar shapes or different shapes. In this manner, the pulses generated by therapy module 34 may be generated to produce pulses of any shape or size. In some examples, electrical stimulation may even be delivered with continuous waveforms or a combination of continuous waveforms and pulses.

Memory 32 may store a plurality of ramp schedules that each define the process for increasing or decreasing a parameter value during delivery of electrical stimulation. The plurality of ramp schedules may be stored in a look-up table or other database. Processor 30 may select the appropriate ramp schedule based on the pulse frequency of selected electrical stimulation, where each ramp schedule may be tagged for used with one or more pulse frequencies (e.g., a single frequency or a band of frequencies). Alternatively, the plurality of ramp schedules may be stored as one or more equations. The one or more equations may establish a relationship between a parameter value and an aspect of the ramp schedule (e.g., the relationship between a pulse frequency and a ramp period for increasing the amplitude or pulse width). In other examples, the one or more equations may be used to output a sequence of parameter values to be used during the ramp period upon entering one or more values of the desired or target parameter set for electrical stimulation.

Each ramp schedule stored in memory 32 may include one or more variables that at least partially define how IMD 14 may increase or decrease a parameter set when delivering electrical stimulation. A ramp schedule may include one or more of a ramp period, a rate at which the parameter value is to be increased or decreased, a matrix describing the relationship of one parameter to another parameter over time, or any other aspects appropriate for ramping one or more parameter values. In some examples, one or more ramp schedules may be altered by a clinician to address the specific condition of patient 12. In other examples, processor 30 may automatically alter a ramp schedule based on patient input when the ramp schedule is used. In other words, patient input indicating that stimulation therapy is undesirable prior to reaching the target amplitude may trigger processor 30 to increase the ramp period or decrease the rate of increase for that particular ramp schedule.

IMD also includes components to receive power from programmer 20 or a separate charging device to recharge a batter of power source 38. Power source 38 may include one or more capacitors, batteries, or other energy storage devices. IMD 14 may thus also include an inductive coil and a recharge module (both not shown) configured to manage the recharging session for power source 38. Although inductive coupling may be used to recharge power source 38, other wireless energy transfer techniques may alternatively be used. Alternatively, power source 38 may not be rechargeable.

Processor 30 may also control the exchange of information with programmer 20 and/or an external programmer using telemetry module 36. Telemetry module 36 may be configured for wireless communication using radio frequency protocols or inductive communication protocols. Telemetry module 36 may include one or more antennas configured to communicate with programmer 20, for example. Processor 30 may transmit operational information and receive therapy programs or therapy parameter adjustments via telemetry module 36. Also, in some examples, IMD 14 may communicate with other implanted devices, such as stimulators, control devices, or sensors, via telemetry module 36. For example, telemetry module 36 may receive user input, ramp schedules, or other commands from programmer 20.

In other examples, IMD 14 may include additional components or modules to perform or assist with certain functionality for techniques and processes described herein. For example, IMD 14 may include one or more accelerometers that detect accelerations of IMD 14 with respect to gravity. The one or more accelerometers may include a single-axis accelerometer or a three-axis accelerometer, for example. Processor 30 may receive output from the accelerometer, such as one or more signals, representative of the acceleration of patient 12. Processor 30 may interpret these signals to distinguish between two or more different posture states. Processor 30 may then modify or adjust one or more parameters, ramp periods, ramp rates, or any other aspect of stimulation therapy disclosed herein. Example posture states may include sitting, standing, lying down, lying face down, lying face up, lying on a side, reclining, walking, running, climbing stairs, riding in an automobile, riding a bike, or any other postures or activities of patient 12.

Figure 4:
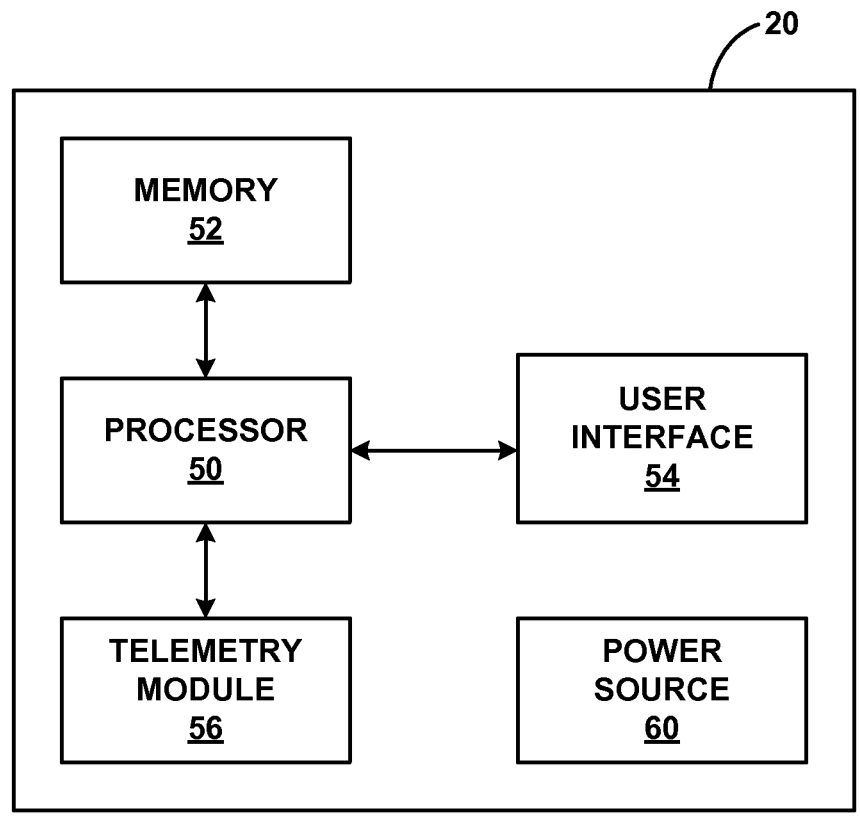
FIG. 4 is a block diagram of the example external programmer of FIGS. 1 and 2.

FIG. 4 is a block diagram of the example external programmer 20. While programmer 20 may generally be described as a hand-held device, programmer 20 may be a larger portable device or a more stationary device. In addition, in other examples, programmer 20 may be included as part of an external charging device or include the functionality of an external charging device. As illustrated in FIG. 4, programmer 20 may include a processor 50, memory 52, user interface 54, telemetry module 56, and power source 60. Memory 52 may store instructions that, when executed by processor 50, cause processor 50 and external programmer 20 to provide the functionality ascribed to external programmer 20 throughout this disclosure. For example, processor 50 may be configured to select a ramp schedule for increasing or decreasing a parameter value during delivery of electrical stimulation.

In general, programmer 20 comprises any suitable arrangement of hardware, alone or in combination with software and/or firmware, to perform the techniques attributed to programmer 20, and processor 50, user interface 54, and telemetry module 56 of programmer 20. In various examples, programmer 20 may include one or more processors, such as one or more microprocessors, DSPs, ASICs, FPGAs, or any other equivalent integrated or discrete logic circuitry, as well as any combinations of such components. Programmer 20 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processor 50 and telemetry module 56 are described as separate modules, in some examples, processor 50 and telemetry module 56 are functionally integrated. In some examples, processor 50 and telemetry module 56 correspond to individual hardware units, such as ASICs, DSPs, FPGAs, or other hardware units.

Memory 52 may store instructions that, when executed by processor 50, cause processor 50 and programmer 20 to provide the functionality ascribed to programmer 20 throughout this disclosure. For example, memory 52 may include instructions that cause processor 50 to obtain a parameter set from memory, select an appropriate ramp schedule, or receive a user input and send a corresponding command to IMD 14, or instructions for any other functionality. In addition, memory 52 may include a plurality of programs, where each program includes a parameter set that defines stimulation therapy, and/or a plurality of ramp schedules. In some examples, programmer 30 may select a ramp schedule when a user provides input to start stimulation. In other examples, IMD 14 may request that programmer 30 selects a ramp schedule and transmits the ramp schedule, or at least one aspect of the ramp schedule, back to IMD 14 for delivery of corresponding electrical stimulation.

User interface 54 may include a button or keypad, lights, a speaker for voice commands, a display, such as a liquid crystal (LCD), light-emitting diode (LED), or cathode ray tube (CRT). In some examples the display may be a touch screen. User interface 54 may be configured to display any information related to the delivery of stimulation therapy, such as currently selected parameter values, ramping curves, ramping schedules, ramp periods, rates of increase or decrease during a ramp, currently held parameter values, or any other therapy information. User interface 54 may also receive user input via user interface 54. The input may be, for example, in the form of pressing a button on a keypad or selecting an icon from a touch screen. The input may request starting or stopping electrical stimulation, the input may be a hold input stopping the increase of amplitude during a ramp, or the input may specify changing an aspect of the ramp schedule.

Telemetry module 56 may support wireless communication between IMD 14 and programmer 20 under the control of processor 50. Telemetry module 56 may also be configured to communicate with another computing device via wireless communication techniques, or direct communication through a wired connection. In some examples, telemetry module 56 may be substantially similar to telemetry module 36 of IMD 14 described herein, providing wireless communication via an RF or proximal inductive medium. In some examples, telemetry module 56 may include an antenna, which may take on a variety of forms, such as an internal or external antenna.

Examples of local wireless communication techniques that may be employed to facilitate communication between programmer 20 and IMD 14 include RF communication according to the 802.11 or Bluetooth specification sets or other standard or proprietary telemetry protocols. In this manner, other external devices may be capable of communicating with programmer 20 without needing to establish a secure wireless connection. As described herein, telemetry module 56 may be configured to transmit a ramp schedule or other stimulation parameter values to IMD 14 for delivery of stimulation therapy.

Figure 5A:
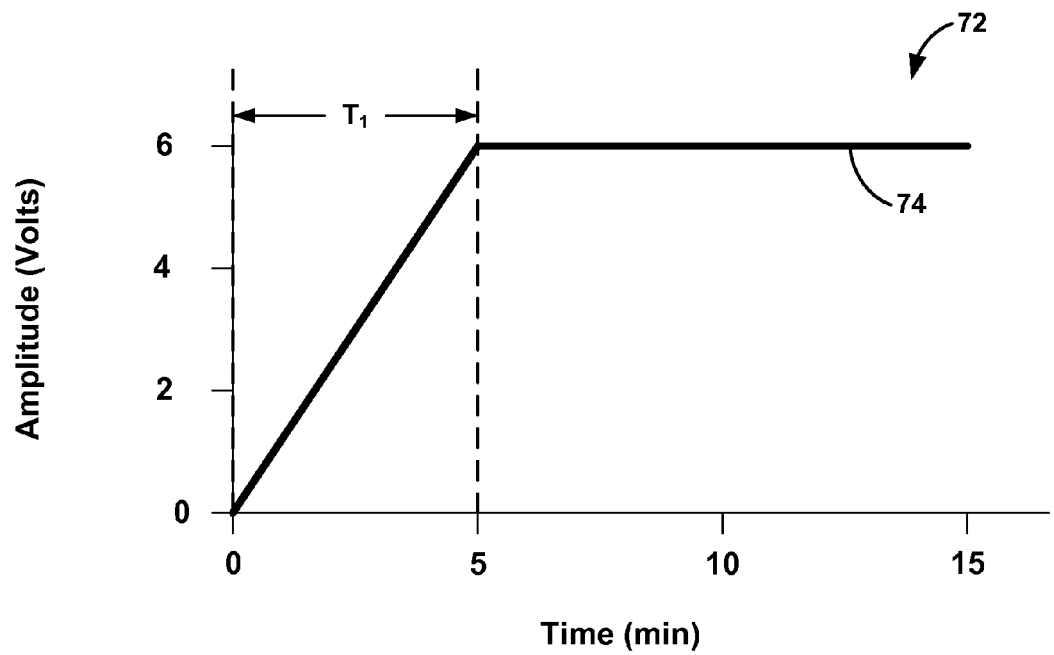
FIGS. 5A and 5B are graphs of example amplitude ramping schedules selected based on a pulse frequency of the electrical stimulation.
Figure 5B:
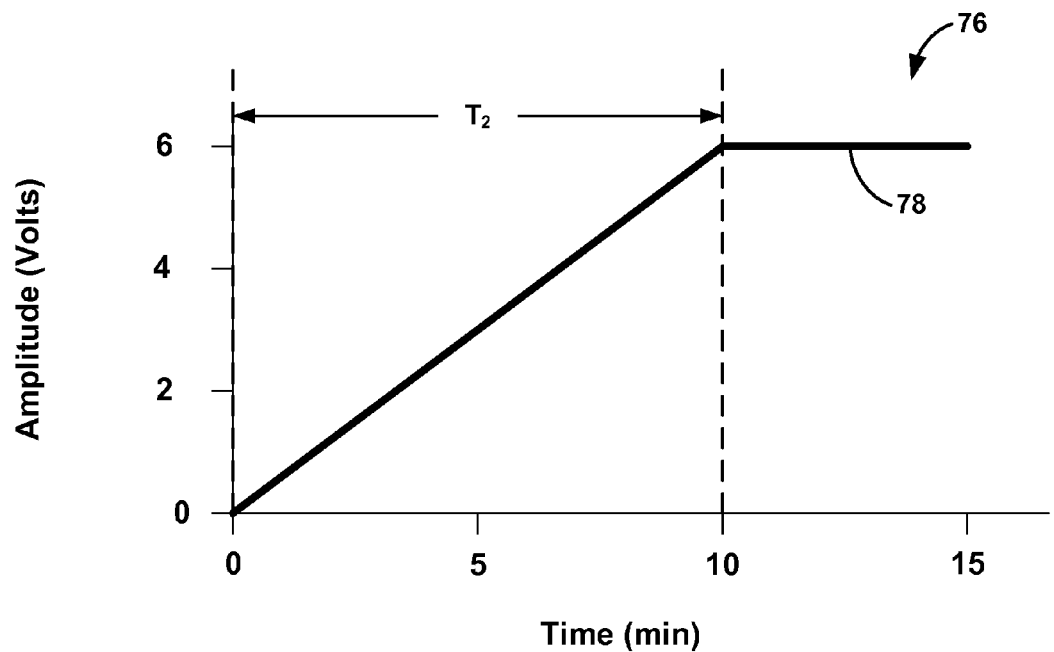

FIGS. 5A and 5B are graphs of example amplitude ramping schedules selected based on a pulse frequency of the electrical stimulation. FIGS. 5A and 5B provide example ramp schedules based on one electrical stimulation parameter set including a 1,000 Hz pulse frequency (FIG. 5A) and another electrical stimulation parameter set including a 6,000 Hz pulse frequency (FIG. 5B). In other words, the amplitude ramp schedule in FIG. 5A is selected for a pulse frequency lower than the pulse frequency of FIG. 5B.

As shown in FIG. 5A, graph 72 illustrates example amplitude values over time when ramping amplitude according to the pulse frequency of the electrical stimulation. A ramp schedule that defines the ramp of amplitude value 74 during the ramp period may be selected based on a pulse frequency of approximately 1,000 Hz (1 kHz). Amplitude value 74 indicates the value of the voltage amplitude with respect to time during and after the ramp period.

At the beginning of electrical stimulation, IMD 14 may obtain the parameter set for electrical stimulation. The pulse frequency may be set as 1,000 Hz and the amplitude may be set to 6.0 volts. However, immediately delivering stimulation pulses at this intensity may provide an undesirable physiological response from patient 12. Therefore, IMD 14 may select a ramp schedule that defines an initial ramp period (e.g., the ramp period of $T_1$) to gradually increase amplitude up to the target stimulation parameter values. IMD 14 may start the ramp at an amplitude of zero volts and linearly increase the amplitude to 6.0 volts over the ramp period of approximately 5 minutes. This ramp period may equal an approximate rate of increase of 1.2 volts per minute. After the ramp period of $T_1$ is finished, IMD 14 may maintain amplitude 74 at 6.0 volts until IMD 14 is commanded to deliver stimulation according to different stimulation parameters or terminate electrical stimulation.

In contrast, FIG. 5B provides graph 76 that illustrates a ramp schedule, and ramp period, based on a higher pulse frequency than that of the stimulation in graph 72. The ramp schedule that defines the ramp of amplitude value 78 during the ramp period may be selected based on a pulse frequency of approximately 6,000 Hz (6 kHz). Amplitude value 78 indicates the value of the voltage amplitude with respect to time during and after the ramp period.

At the beginning of electrical stimulation, IMD 14 may obtain the parameter set for electrical stimulation. The pulse frequency may be set as 6,000 Hz and the amplitude may be set to 6.0 volts. IMD 14 may thus select a ramp schedule that defines an initial ramp period (e.g., the ramp period of $T_2$) to gradually increase amplitude from an initial value up to the target stimulation parameter values. IMD 14 may start the ramp at an amplitude of zero volts and linearly increase the amplitude to 6.0 volts over the ramp period of approximately 10 minutes. This ramp period may equal an approximate rate of increase of 0.6 volts per minute. Therefore, the increased pulse frequency of stimulation in FIG. 5B has caused IMD 14 to select a ramp period $T_2$ greater than $T_1$ that results in a lower rate of amplitude increase during the ramp period than that of the stimulation in FIG. 5A. After the ramp period of $T_2$ is finished, IMD 14 may maintain amplitude 78 at 6.0 volts until IMD 14 is commanded to deliver stimulation according to different stimulation parameters or terminate electrical stimulation. Although the target amplitudes of FIGS. 5A and 5B were equivalent, longer ramp periods and/or lower amplitude increase rates may be used for higher pulse frequencies even if the target amplitudes are different.

Amplitude values may continually increase over time according to the selected ramp schedule. However, ramping up, or increasing, an amplitude (or other parameter) may generally refer to the overall direction of change to the amplitude. For example, the amplitude may increase and decrease during the ramp period while generally trending toward higher amplitudes. In this manner, an increase ramp may include amplitudes that undulate (e.g., increase amplitude and decrease amplitude) over time. This undulation may be in the form of a wave-like ramp or a saw-tooth ramp. Incorporating some decreases in amplitude when ramping up may be perceived as more comfortable or tolerable by patient 12.

The ramp periods of FIGS. 5A and 5B may be fixed to a predetermined duration for each pulse frequency or band of pulse frequencies. In other examples, the ramp periods may be variable based on starting at non-zero amplitudes, different target amplitudes, patient input requesting a pause in the increase in amplitudes, or predetermined increase rates for amplitude. For example, the increase rate for amplitude change may be predetermined for one or more pulse frequencies. The ramp period may thus run until the target amplitude is reached using the predetermined increase rate.

In other examples, patient 12 or the clinician may select a ramp schedule, increase rate, or ramp period from a set of options presented by programmer 20. These user selected options may allow therapy to be customized for a specific patient. In one example, programmer 20 may present a set of options for one or more ramp schedules. Programmer 20 may provide abstract options that generally relate to how fast the ramp will occur. For example, these options may be presented generally as "gradual," "moderate," and "aggressive." Programmer 20 or IMD 14 may automatically select ramp schedules based on the user selection. In other words, increase rates may be higher for an "aggressive" selection and lower for a "gradual" selection. In other examples, the options may be more specific. For example, programmer 20 may present two or more different ramp period durations and/or increase rates for one or more pulse frequencies. Programmer 20 may receive the option selection from the user and update the ramp schedules accordingly.

Although amplitudes are ramped linearly in FIGS. 5A and 5B, non-linear ramping schedules may be used in other examples. For example, a ramp schedule may define an increase or decrease in parameter values that is exponential, logarithmic, polynomial, step-wise, or any combination thereof. In addition, ramp schedules may be based on the desired amplitude in addition to the pulse frequency of the parameter set. Since higher amplitudes may be perceived as higher intensity stimulation, the ramp schedule may increase the ramp period for higher amplitudes even if the pulse frequency is equal. This increased ramp period may be set to maintain a rate of increase during the ramp period or even decrease the rate of increase to achieve the higher target amplitude values.

Figure 6A:
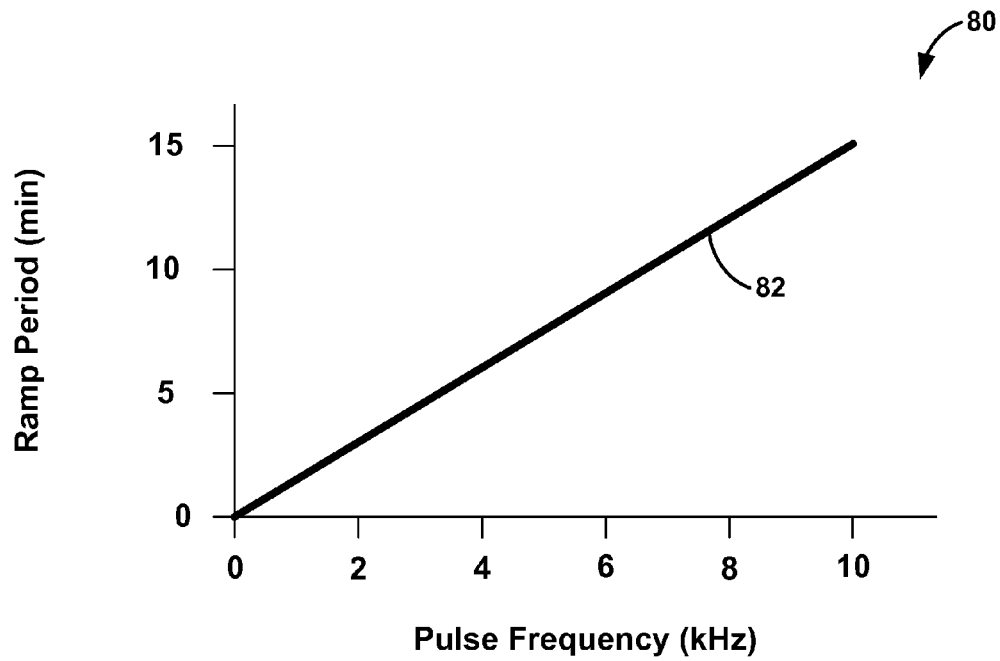
FIGS. 6A and 6B are graphs of example relationships between pulse frequency and amplitude ramp period for delivering electrical stimulation.
Figure 6B:
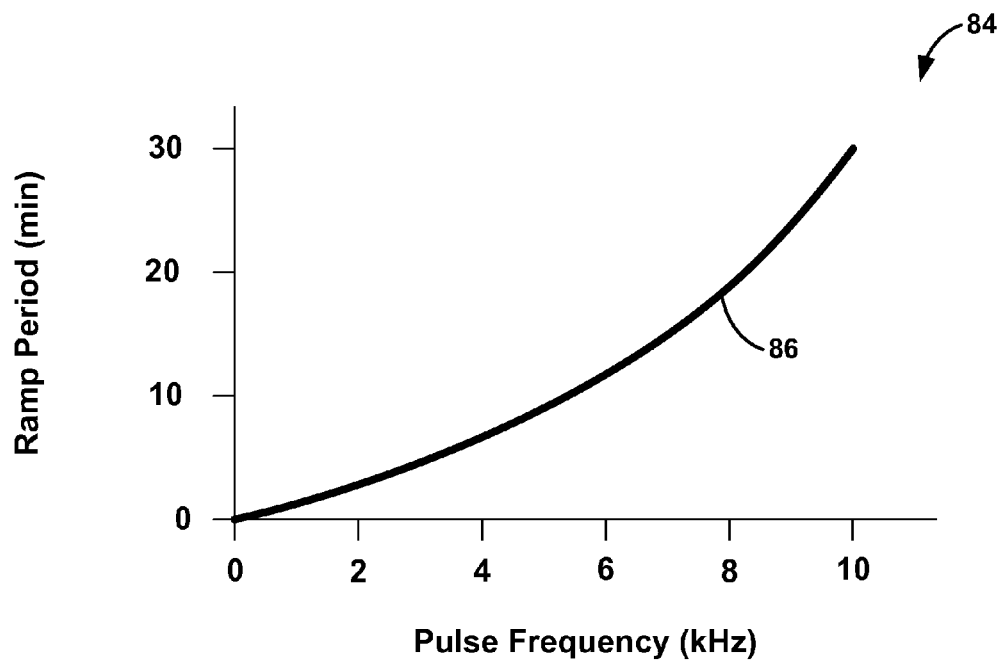

FIGS. 6A and 6B are graphs of example relationships between pulse frequency and amplitude ramp period for delivering electrical stimulation. As shown in FIG. 6A, graph 80 illustrates an example relationship between a ramp period of a selected ramp schedule and the pulse frequency of the electrical stimulation. Line 82 indicates that the relationship between ramp period and pulse frequency is approximately linear. For example, ramp periods for increasing amplitude may be directly proportional to the pulse frequency of the electrical stimulation. Line 82 may represent a relationship that may also be described by an equation. The equation may be $P=X*F$, where F is the pulse frequency in Hz, P is the ramp period in minutes, and X is the multiplier variable indicating the slope of line 82. In the example of FIG. 6A, X may be approximately 0.0015. In other examples, X may be generally between approximately 0.01 and 0.0005. However, the multiplier may be smaller or greater in some examples.

As shown in FIG. 6B, graph 84 illustrates an alternative relationship between a ramp period of a selected ramp schedule and the pulse frequency of the electrical stimulation. Line 86 indicates that the relationship between ramp period and pulse frequency may be approximately exponential. In this manner, higher pulse frequencies may call for ever increasing ramp periods to allow patient 12 get accustomed to the higher pulse frequencies. In the example relationship of graph 84, a ramp period of approximately one minute may be used for a pulse frequency of approximately 1,000 Hz and a ramp period of approximately 30 minutes may be used for a pulse frequency of approximately 10,000 Hz. However, exponential curves like that of line 86 may be increased or decreased to adjust how IMD 14 and/or programmer 20 selects a ramp period based on the pulse frequency.

The relationship between ramp period and pulse frequency may be described alternatively from a linear or exponential relationship. For example, line 84 may instead represent a relationship that is logarithmic, polynomial, step-wise, or any combination thereof. In other examples, a relationship between the pulse frequency and rate of increase may be defined. Since the rate of increase for a particular ramp schedule may be inversely proportional to the ramp period, the relationship between a rate of increase and pulse frequency may be similarly inverse to that of graphs 80 and 84.

Figure 7A:
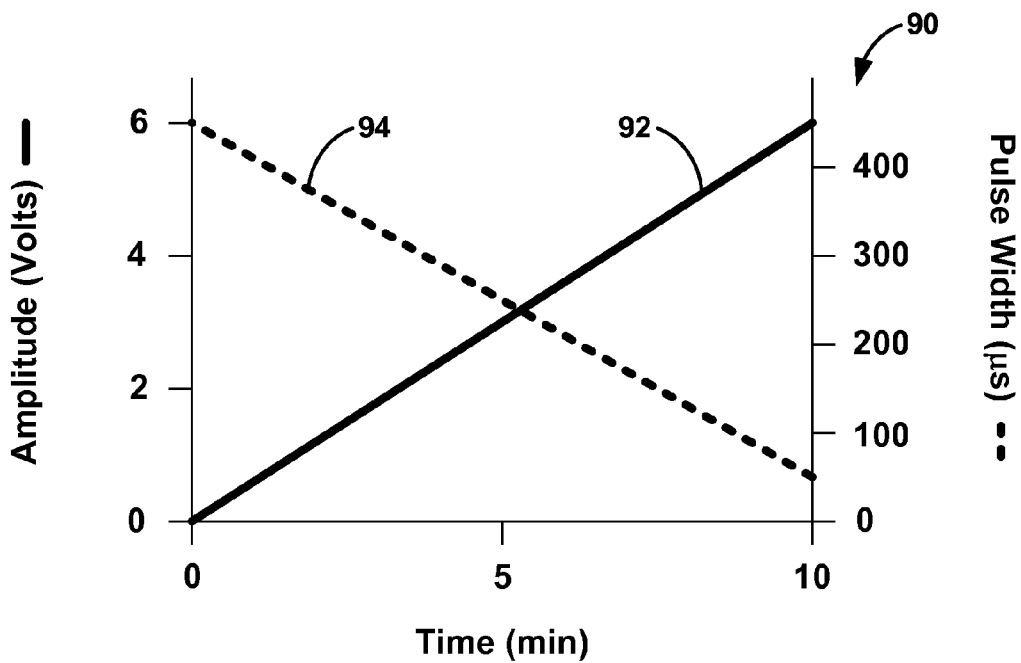
FIG. 7A is a graph of an example amplitude ramping schedule and pulse width ramping schedule for delivering electrical stimulation.

FIG. 7A is a graph of an example amplitude ramping schedule 92 and pulse width ramping schedule 94 for delivering electrical stimulation. IMD 14 may ramp amplitude concurrently with pulse width when delivering electrical stimulation. As described herein, ramping one parameter up (e.g., amplitude) while ramping another parameter down (e.g., pulse width), may increase paresthesia to a particular region of patient 12 without increasing the size of the region in the patient.

As shown in FIG. 7A, IMD 14 and/or programmer 20 has selected amplitude ramping schedule 92 and pulse width ramping schedule 94 to define how each stimulation parameter will change in value over time. At the zero minute mark, or the beginning of the ramp period for each parameter, IMD 14 may deliver electrical stimulation with an amplitude of approximately zero volts and a pulse width of approximately 450 milliseconds (μs). As time increases, IMD 14 may increase the amplitude value according to amplitude ramp schedule 92. Concurrently, IMD 14 may decrease the pulse width value according to pulse width ramp schedule 94. After a ten minute ramp period, IMD 14 may maintain delivery of electrical stimulation with an amplitude of approximately 6.0 volts and a pulse width of approximately 50 μs.

The ramp period for increasing the amplitude and decreasing the pulse width is shown as equal and completely overlapping. In other examples, the ramp period for one of the amplitude or pulse width may begin and/or end at different times than the other parameter. However, the ramp period for each parameter may overlap for at least a portion of time (e.g., one or more pulses). The ramp period of 10 minutes is one example, but the period for concurrent ramping of two parameters may be smaller or greater than 10 minutes in other examples. In addition, the amplitude and pulse width values may be different in other examples, according to the parameter values described herein.

In addition, amplitude ramp schedule 92 and/or pulse width ramp schedule 94 may define a linear, or non-linear relationship in other examples, and may increase or decrease in parameter values. For example, amplitude ramp schedule 92 and/or pulse width ramp schedule 94 may be exponential, step-wise, or a combination of any type of relationship. In some examples, the ramp schedule of one parameter may be at least partially based on the ramp schedule for another parameter. IMD 14 may first select amplitude ramp schedule 92, for example. Then, IMD 14 may select pulse width ramp schedule 94 based on the starting and target amplitude values of amplitude ramp schedule 92. In this manner, IMD 14 may customize or otherwise select additional ramp schedules such that the overall stimulation therapy is appropriate for patient 14.

FIG. 7A illustrates an example in which IMD 14 may ramp a different pair of parameters than amplitude and pulse width. For example, IMD 14 may concurrently ramp any pair of amplitude, pulse width, or pulse frequency. In other examples, IMD 14 may only ramp pulse width over time when delivering electrical stimulation. IMD 14 may select a pulse width ramp schedule to increase or decrease pulse width over a ramp period. This ramp of pulse width may be used to gradually change the nerve fibers affected by the electrical stimulation.

Figure 7B:
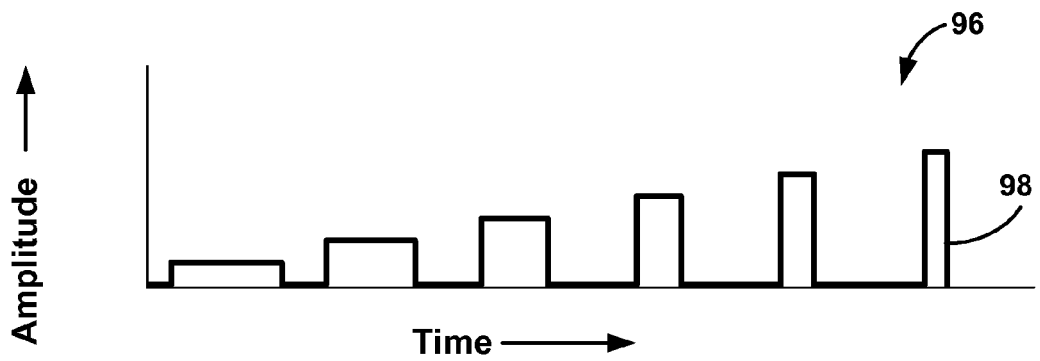
FIGS. 7B and 7C are example timing diagrams of ramping pulse width down and ramping pulse width up.
Figure 7C:
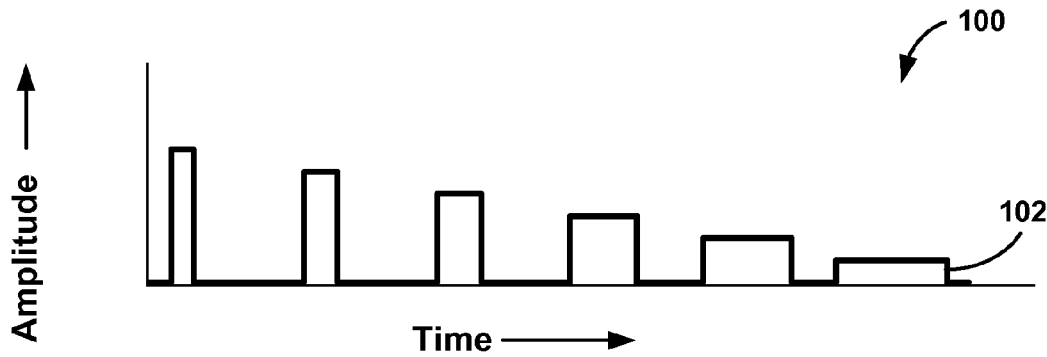

FIGS. 7B and 7C are example timing diagrams 96 and 100, respectively, of ramping pulse width down and ramping pulse width up. As shown in FIG. 7B, timing diagram 96 illustrates that pulses 98 are changed over time according to the concurrent ramping of amplitude and pulse width shown in FIG. 7A. Each consecutive pulse delivered by IMD 14 may increase in amplitude according to the amplitude ramp schedule and decrease in pulse width according to the pulse width ramp schedule. In other examples, each consecutive pulse 98 may change only one of the parameter values from the previous pulse. For example, each consecutive pulse may alternate between increasing amplitude and decreasing pulse width. This alternating ramping may still be considered concurrent ramping with multiple parameters.

Alternatively, IMD 14 may ramp one or both parameters without making changes to the parameter value in each consecutive pulse. For example, IMD 14 may deliver two or more pulses defined by the same parameter values before IMD 14 changes one or both of the ramping parameters. In this manner, an increasing ramp and/or a decreasing ramp may include consecutively non-changing pulses to provide more gradual changes to the parameter.

As shown in FIG. 7C, timing diagram 100 illustrates that pulses 102 are changed over time according to an inverse in the concurrent ramping of amplitude and pulse width of FIG. 7A. Timing diagram 100 indicates that pulses 102 may decrease in amplitude over time concurrently with an increase in pulse width over time. This concurrent ramping may provide electrical stimulation that decreases the strength of paresthesia while maintaining the general area of patient 12 in which patient 12 perceives the paresthesia.

FIGS. 8A, 8B, 9A, and 9B are graphs of example iterative amplitude ramping to achieve elevated electrical stimulation intensities for patient therapy. Iterative ramping may refer to a gradual process in which a stimulation parameter value is ramped over time (e.g., tens of minutes, hours, or days) to slowly increase the stimulation intensity that would be acceptable to patient 14. IMD 14 may increase a parameter, such as amplitude, in multiple ramp periods over time in an attempt to achieve higher stimulation intensities and efficacious stimulation therapy for the patient. Subsequent ramp periods may begin at a previous maximum value resulting from the end of the previous ramp or below the previous maximum value and increase past the previous maximum value. Ramp periods may be paused or terminated when IMD 14 and/or programmer 20 receives a hold input from patient 12.

Figure 8A:
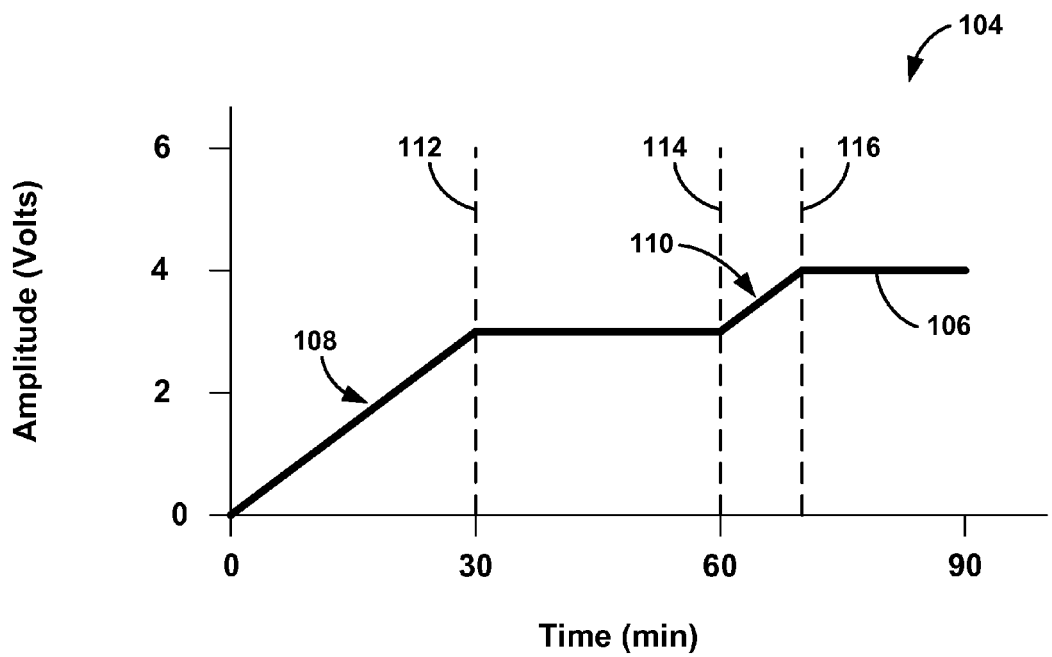
FIGS. 8A, 8B, 9A, and 9B are graphs of example iterative amplitude ramping to achieve elevated electrical stimulation intensities for patient therapy.

As shown in FIG. 8A, graph 104 illustrates the change in amplitude 106 during an iterative ramping process. IMD 14 and/or processor 20 may select a ramp schedule for iterative ramping over time. Ramp schedule 108 may define the increase in amplitude during the first ramp period between 0 minutes and 30 minutes. Hold input 112 may be received by programmer 20 and IMD 14 at approximately the 30 minute time point. In response to receiving hold input 112, IMD 14 may maintain the electrical stimulation at the amplitude of approximately 3.0 volts for a period of time. The period of time may be a predetermined period of time after hold input 112 is received or equal to the duration of which the user depresses or provides hold input 112. Alternatively, the period of time may be an open-ended period that continues until IMD 14 receives a request from patient 12 to change stimulation parameters or terminate stimulation or until IMD 14 changes a stimulation parameter value in response to a detected physiological change in patient 12 or other received instruction.

In response to receiving ramp request 114, IMD 14 may begin subsequent ramp schedule 110 to once again ramp up amplitude 106. Ramp request 114 may be in the form of an input received from patient 12 or another user. Alternatively, ramp request 114 may be a command triggered based on the amount of time amplitude 106 has been maintained. In other words, IMD 14 and/or programmer 20 may include instructions that automatically restart ramping. When IMD 14 and/or programmer 20 receives hold input 116, IMD 14 may again hold or maintain amplitude 106 at the current amplitude value (e.g., approximately 4.0 volts). IMD 14 may then continue to deliver electrical stimulation at the hold amplitude value, e.g., the maximum amplitude value tolerable by patient 12.

During iterative ramping, a ramp schedule may be selected such that the ramp period for a continuous ramp (e.g., ramp schedule 108 and 110) is on the order of minutes, hours, or even days. For example, a single continuous ramp period during the iterative ramping process may be between approximately 20 minutes and 90 minutes. However, single ramp periods may be less than 20 minutes when the ramp is terminated by a hold input from patient 12. Alternatively, the single ramp period may be longer than 90 minutes when patient 12 does not provide a hold input.

IMD 14 and/or programmer 20 may store instructions for the iterative ramping process. Iterative ramping may continue for a specified number of ramps, at a predetermined frequency, until a predetermined maximum value is reached, and/or a termination input is received from patient 12. Alternatively, IMD 14 or programmer 20 may automatically terminate the iterative ramping process when hold inputs are receives within a predetermined amount of time from the beginning of the ramp or within a predetermined change in the amplitude value. The timing of these inputs may indicate that the stimulation amplitude, or intensity, has reached a maximum amplitude for patient 14. In some examples, IMD 14 and/or programmer 20 may re-start the iterative ramping process after a predetermined amount of time (e.g., a day, week, or month) has elapsed since the previous iterative ramping process was terminated or in response to receiving a re-start request from the user.

In some examples, such as the example shown in graph 104 of FIG. 8A, each ramp schedule may define the same rate of increase for the parameter. In other examples, the rate of increase may vary between ramp periods of the iterative ramping process. Subsequent ramp periods may include lower rates of increase than previous ramp periods. More gradually increasing the parameter value in subsequent ramp periods may allow the parameter to achieve higher values (e.g., higher stimulation intensities) by enabling patient 12 to acclimatize to the increased values.

Figure 8B:
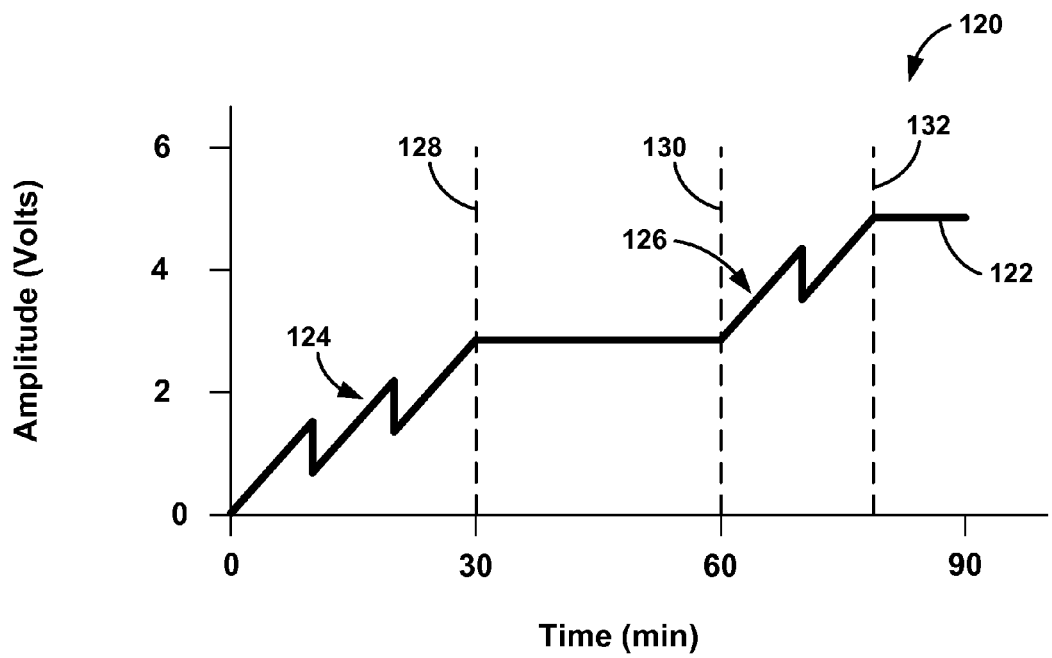

As shown in FIG. 8B, graph 120 is substantially similar to graph 104 of FIG. 8A. However, graph 120 illustrates ramp periods that include a non-linear ramp schedule. In the example of FIG. 8B, ramp schedules 124 and 126 may be saw-tooth ramps for increasing amplitude 122 as a part of the iterative ramping process. A saw-tooth ramp may describe a ramp schedule in which the amplitude is increased to a first value, then decreased to a second value, and increased again to a value greater than the first value. In other words, the saw-tooth ramp schedule may provide an oscillating amplitude ramp or quasi-step-wise amplitude ramp that toggles between increasing and decreasing amplitude to gradually increase amplitude over time.

Each "tooth" of the saw-tooth ramp may be defined as to the duration of each tooth, the rate of increase in the tooth and the rate of decrease in the tooth. As shown in graph 120, the rate of increase is gradual and the rate of decrease is instantaneous or immediate. Alternatively, the rates of increase and decrease may each be gradual, slightly different, or even equal. Although ramp schedule 124 indicates that only three "teeth" may be provided within a 30-minute ramp period, a ramp period may include more frequent or less frequent teeth of the saw-tooth ramp. For example, each "tooth," or increase and decrease pair, may include a time period between approximately 0.5 seconds and 30 minutes. Shorter and longer teeth may be provided in other examples.

Once IMD 14 selects ramp schedule 124, ramp schedule 124 may define the saw-tooth increase in amplitude during the first ramp period between 0 minutes and 30 minutes. Hold input 128 may be received by programmer 20 and IMD 14 at approximately the 30 minute time point. In response to receiving hold input 128, IMD 14 may maintain the electrical stimulation at the amplitude of approximately 3.0 volts. In response to receiving ramp request 130, IMD 14 may begin subsequent ramp schedule 126, another saw-tooth ramp, to once again ramp amplitude 122 up. When IMD 14 and/or programmer 20 receives hold input 132 at approximately 80 minutes, IMD 14 may again hold or maintain amplitude 122 at the current amplitude value (e.g., approximately 4.6 volts). IMD 14 may then continue to deliver electrical stimulation at the hold amplitude value, e.g., the maximum amplitude value tolerable by patient 12.

Although ramp schedules 124 and 126 are both described as saw-tooth ramps, each ramp schedule of the iterative ramp process may not utilize the same ramp profile. Instead, different ramp periods may utilize different ramp profiles. These different ramp profiles may be selected based on the beginning amplitude of the ramp period or other variables. For example, a saw-tooth ramp may be used at higher amplitudes and an exponential ramp may be used to begin stimulation or at lower amplitudes.

In another example, iterative ramping may be performed by ramping current amplitude. IMD 14 may begin by delivering stimulation with a comfortable amplitude for patient 12 (e.g., 2.0 mA). IMD 14 may also set a maximum amplitude for the ramp period (e.g., 5.0 mA). IMD 14 may then select a ramp period. The ramp period may be selected to be between 20 minutes and 90 minutes, such as approximately 60 minutes. IMD 14 may also select the ramp type (e.g., linear or non-linear) and rate of increase, such as approximately 0.083 mA per minute. Example ranges for the rate of increase may be between approximately 0.01 mA per minute and 0.5 mA per minute. The ramp period and rate of increase may be defined by a single ramp schedule.

Once IMD 14 begins ramping up the amplitude, programmer 30 and/or IMD 14 may receive a hold input that indicates the user would like to stop the ramp. The hold input may indicate that the amplitude may be becoming uncomfortable or otherwise at the tolerable maximum. If IMD 14 reaches the maximum amplitude for the ramp period without receiving a hold input, IMD 14 instructs programmer 20 to present a notification to patient 12 that the ramp has been completed. This notification may be in the form of a light, audible sound, tactile vibration, text message presented on the user interface, or any other presentation type. In some examples, IMD 14 may learn how much of an amplitude change patient 12 can tolerate in a given time period and suggest new ramp schedules to accommodate the patient-specific tolerances. The tolerable amplitude change may be based on previously used amplitude ramp rates, the difference between starting amplitude values and hold amplitude values for respective ramp periods, or the use of any other data related to previously used ramp schedules. Programmer 20 may present the new ramp schedules to the user for selection or automatically select the new ramp schedules.

Figure 9A:
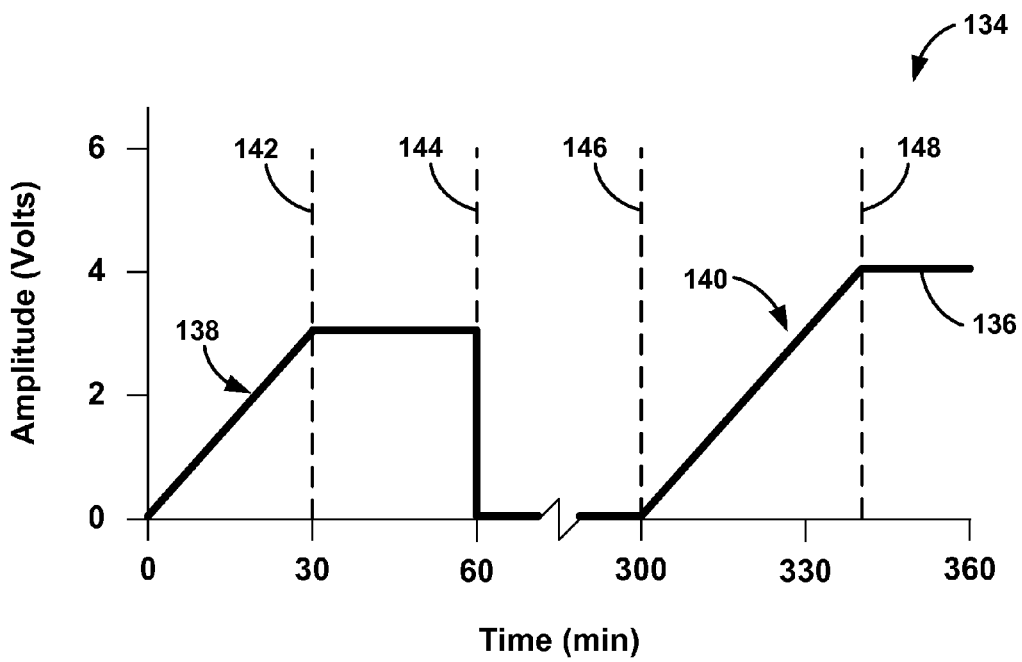

FIG. 9A may be similar to FIG. 8A. However, IMD 14 may continue the iterative ramping process after electrical stimulation has been turned off or different stimulation parameters (e.g., different therapy programs) were used to define electrical stimulation. As shown in FIG. 9A, graph 134 illustrates the change in amplitude 136 during an iterative ramping process. The iterative ramping process may be a non-continuous iterative ramping process because the delivery of electrical stimulation according to a particular parameter set (e.g., a unique therapy program) may be broken or interrupted by different parameter sets or a lack of any electrical stimulation. IMD 14 and/or processor 20 may select a ramp schedule for iterative ramping over time. Ramp schedule 138 may define the increase in amplitude 136 during the first ramp period between 0 minutes and 30 minutes. Hold input 142 may be received by programmer 20 and/or IMD 14 at approximately the 30 minute time point. In response to receiving hold input 142, IMD 14 may maintain the electrical stimulation at the amplitude of approximately 3.0 volts. IMD 14 and/or programmer 20 may also store the amplitude as a hold amplitude value. In response to change command 144, IMD 14 may terminate stimulation or adjust electrical stimulation to be defined by a different parameter set.

After any amount of time, IMD 14 may once again receive a command to deliver the electrical stimulation again. In response to receiving ramp request 146, such as a request to re-start stimulation, IMD 14 may begin to increase amplitude 136 during ramp schedule 140 from approximately zero amplitude or another minimal amplitude value. This minimal amplitude may be lower than the hold amplitude value achieved by the previous ramp schedule 138. Ramp request 146 may be in the form of an input received from a user or patient 12. Alternatively, ramp request 146 may be a command triggered based on a detected patient condition or amount of time from change command 144. In other words, IMD 14 and/or programmer 20 may include instructions that automatically restart ramping. When IMD 14 and/or programmer 20 receives hold input 148, IMD 14 may again hold or maintain amplitude 136 at the current amplitude value (e.g., approximately 4.1 volts). IMD 14 may then store this amplitude as a new hold amplitude value and continue to deliver electrical stimulation at the hold amplitude value, e.g., the maximum amplitude value tolerable by patient 12. The new hold amplitude value may replace the previous hold amplitude value stored after receiving hold input 142. In other examples, IMD 14 and/or programmer 20 may retain all stored hold amplitude values and only refer to the most recent value. The iterative ramping process of graph 134 may continue indefinitely or until a user or patient 12 requests that the iterative ramping be terminated.

Figure 9B:
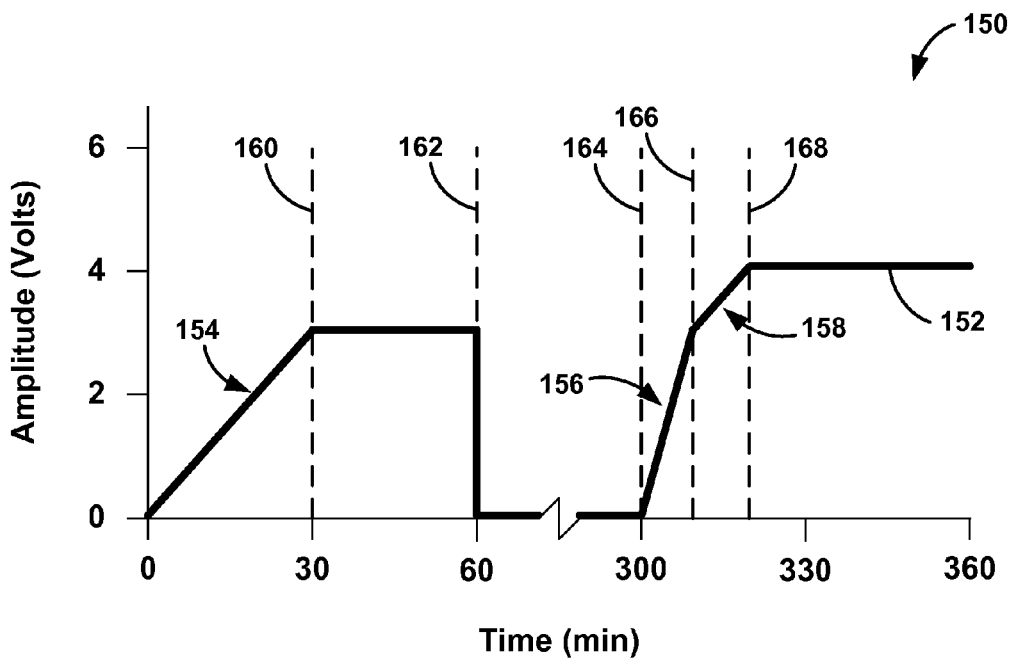

FIG. 9B may be similar to FIG. 9A. However, IMD 14 may select ramp schedules that more quickly increase amplitude until the hold amplitude value is reached. In other words, IMD 14 may select one ramp schedule that defines longer ramp periods and/or lower amplitude increase rates for delivering electrical stimulation with previously unused amplitude values. IMD 14 may select a different ramp schedule that defines shorter ramp periods and/or higher amplitude increase rates for delivering electrical stimulation with amplitudes already used amplitude values. In this manner, IMD 14 may select more gradual amplitude ramping when attempting to increase the tolerable amplitude for patient 14.

As shown in FIG. 9B, graph 150 illustrates the change in amplitude 152 during an iterative ramping process. The iterative ramping process may be a non-continuous iterative ramping process, similar to that of FIG. 9A, because the delivery of electrical stimulation according to a particular parameter set may be broken or interrupted by different parameter sets or a lack of any electrical stimulation. IMD 14 and/or processor 20 may select a ramp schedule for iterative ramping over time. Ramp schedule 154 may define the increase in amplitude 152 during the first ramp period between 0 minutes and 30 minutes. Hold input 160 may be received by programmer 20 and/or IMD 14 at approximately the 30 minute time point. In response to receiving hold input 160, IMD 14 may maintain the electrical stimulation at the amplitude of approximately 3.0 volts. IMD 14 and/or programmer 20 may also store the amplitude as a hold amplitude value. In response to change command 162, IMD 14 may terminate stimulation or adjust electrical stimulation to be defined by a different parameter set.

After any amount of time, IMD 14 may once again receive a command to deliver the electrical stimulation. In response to receiving ramp request 164, such as a request to re-start stimulation, IMD 14 may begin to increase amplitude 152 during ramp schedule 156 from approximately zero amplitude or another minimal amplitude value. Ramp schedule 156 may be significantly different than ramp schedule 154. Since the amplitudes between zero and 3.0 volts (e.g., the previously stored hold amplitude value) are known to be tolerable for patient 14, the ramp through these amplitudes may be at a greater rate than that of ramp schedule 154. In other words, ramp schedule 156 may define a shorter ramp period and/or a higher amplitude increase rate than used previously for ramping from zero (or small, non-zero amplitude) through the previous hold amplitude level. Therefore, IMD 14 may minimize the period of time during which electrical stimulation may not be effective in treating patient 14.

Once the amplitude has increased to the previous hold amplitude level at ramp change 166, IMD 14 may select a slower or more gradual ramp schedule 158 similar to that of ramp schedule 154. This more gradual ramp schedule 158 may be used in an attempt to slowly increase the amplitude and stimulation intensity in a manner tolerable to patient 12. In response to receiving hold input 168, IMD 14 may stop ramping amplitude 152 and hold the amplitude value at the hold amplitude value (e.g., approximately 4.1 volts). IMD 14 and/or programmer 20 may then store this amplitude as a new hold amplitude value and continue to deliver electrical stimulation at the hold amplitude value, e.g., the maximum amplitude value tolerable by patient 12. The new hold amplitude value from hold input 168 may replace the previous hold amplitude value corresponding to hold input 160. In other examples, IMD 14 and/or programmer 20 may retain all stored hold amplitude values and only refer to the most recent value. The iterative ramping process of graph 150 may continue indefinitely or until a user or patient 12 requests that the iterative ramping be terminated.

In other examples, subsequent ramp schedules such as ramp schedule 158 may define increasingly longer ramp periods and/or increasingly lower amplitude increase rates. As the hold amplitude value creeps higher to provide elevated stimulation intensities, IMD 14 may need to increase the amplitude at slower rates in order for the increasing amplitudes to be tolerable. Each iterative ramping process may include specific instructions that define how the ramp schedule is to be modified for each subsequent ramp schedule. Alternatively, IMD 14 may alter subsequent ramping schedules during iterative ramping processes when hold inputs are received relatively soon after a ramp period has started or when the hold amplitude value approaches anticipated tolerable limits for patient.

In any of the iterative ramping processes of FIG. 8A, 8B, 9A, or 9B, any type of parameter value ramp may be used to increase or decrease the parameter value. For example, the ramp may be linear, non-linear, saw-tooth, exponential, logarithmic, polynomial, step-wise, or any combination thereof. Using these ramping techniques, a clinician may select the specific ramping technique that may provide efficacious therapy to patient 14. In some examples, IMD 14 and/or programmer 20 may automatically select one or more ramp schedules based on parameter set values, patient-specific information, or electrical stimulation trends.

In other examples, the fast ramp (e.g., ramp schedule 156) may not be used to increase the amplitude completely to the previous hold amplitude value. Instead, the fast ramp may be used to increase the amplitude to an amplitude lower than the hold amplitude value. The lower amplitude may be a percentage of the hold amplitude value or an absolute unit value lower than the hold amplitude value. IMD 14 may then utilize a slower ramp (e.g., ramp schedule 158) to approach and surpass the hold amplitude value.

Figure 10:
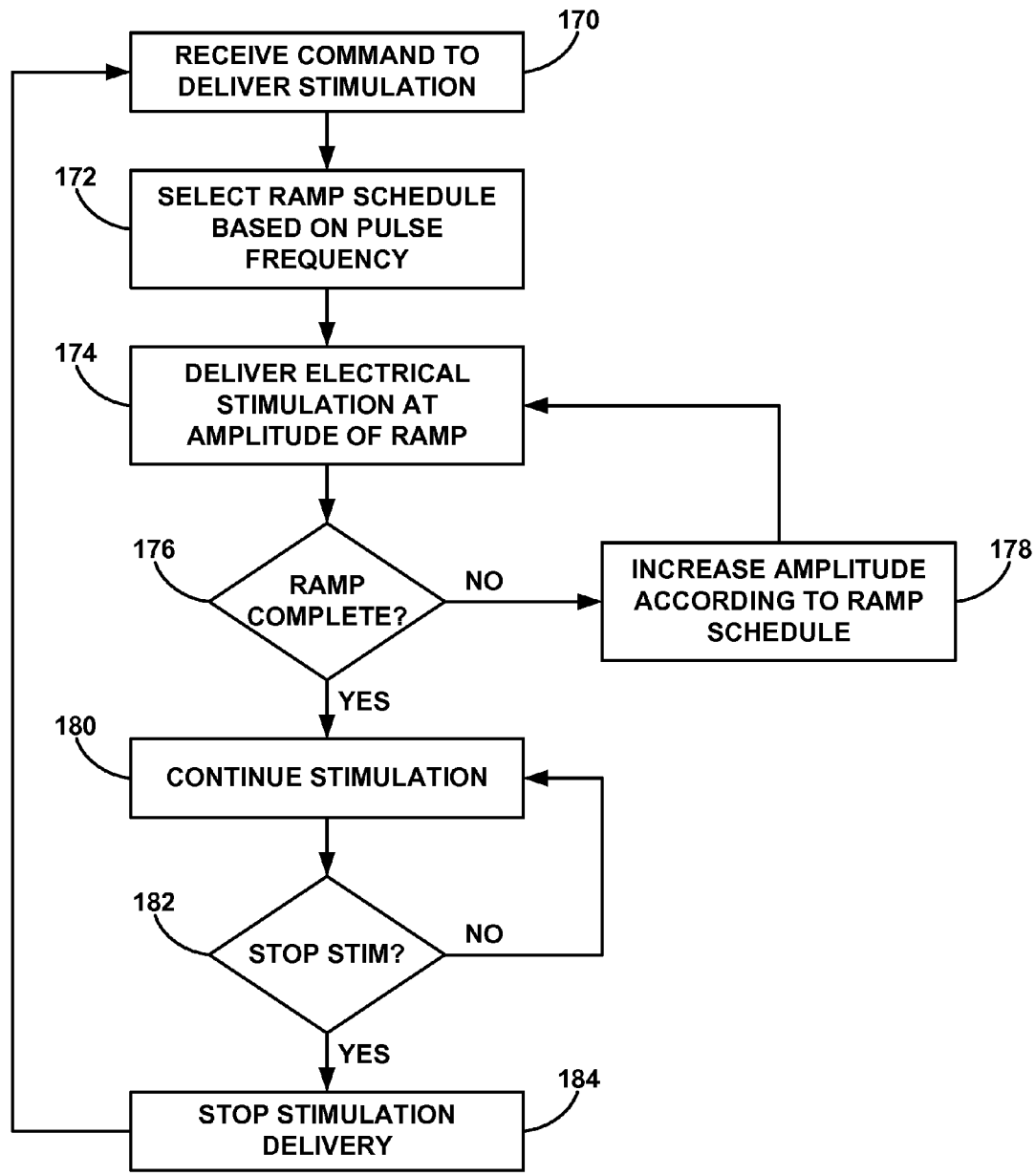
FIG. 10 is a flow diagram that illustrates an example process for selecting an amplitude ramp schedule based on a pulse frequency of the electrical stimulation.

FIG. 10 is a flow diagram that illustrates an example process for selecting an amplitude ramp schedule based on a pulse frequency of the electrical stimulation. Although processor 30 of IMD 14 will be described as generally performing the technique of FIG. 10, the technique of FIG. 10 may instead be performed by a combination of processors 30 and 50 of programmer 20, or only processor 50, in other examples.

As shown in FIG. 10, processor 30 may receive a command to deliver electrical stimulation to patient 14 (170). The command may be in the form of an input to programmer 20 that is transmitted to IMD 14 or an automated command based on a detected signal or time from instructions stored in memory 30. Processor 30 may then select a ramp schedule based on the pulse frequency of the electrical stimulation to be delivered (172). For example, processor 30 may select greater ramp periods (e.g., more gradual amplitude increases) for higher pulse frequencies. The pulse frequency value may be defined by the parameter set of the electrical stimulation. Once processor 30 selects the ramp schedule, processor 30 may begin to deliver electrical stimulation therapy at the starting amplitude of the ramp period defined by the selected ramp schedule (174).

If processor 30 determines that the ramp period is not complete ("NO" branch of block 176), processor 30 may increase the amplitude value according to the ramp schedule (178). Processor 30 may then deliver electrical stimulation with the increased amplitude value (174). If processor 30 determines that the ramp period is complete ("YES" branch of block 176), processor 30 may continue stimulation with the current amplitude value and the other parameter values (180). If processor 30 does not receive a command to stop stimulation ("NO" branch of block 182), processor 30 may continue to deliver electrical stimulation (180). In response to receiving a command to stop stimulation ("YES" branch of block 182), processor 30 may stop delivery of the electrical stimulation therapy (184). Processor 30 may again deliver stimulation upon receiving a command (170).

Figure 11:
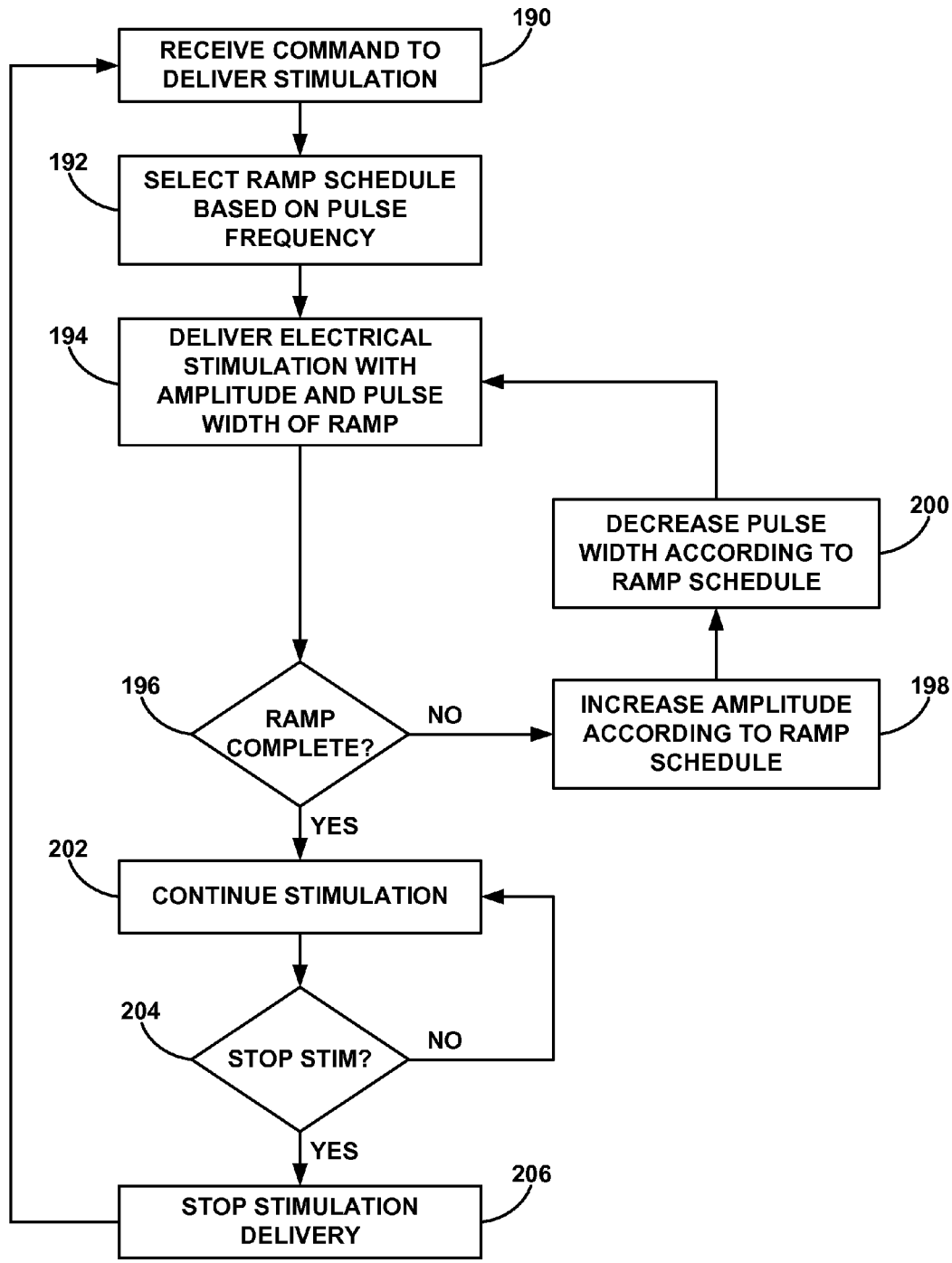
FIG. 11 is a flow diagram that illustrates an example process for selecting a ramp schedule for concurrently ramping amplitude and pulse width.

FIG. 11 is a flow diagram that illustrates an example process for selecting a ramp schedule for concurrently ramping amplitude and pulse width. FIG. 11 may be similar to the process of FIG. 10. Although processor 30 of IMD 14 will be described as generally performing the technique of FIG. 11, the technique of FIG. 11 may instead be performed by a combination of processors 30 and 50 of programmer 20, or only processor 50, in other examples. Concurrent ramping the amplitude up and pulse width down may increase the intensity of the paresthesia of inhibition of affected nerve while limiting the area of patient 14 affected by the stimulation.

As shown in FIG. 11, processor 30 may receive a command to deliver electrical stimulation to patient 14 (190). The command may be in the form of an input to programmer 20 that is transmitted to IMD 14 or an automated command based on a detected signal or time from instructions stored in memory 30. Processor 30 may then select a ramp schedule based on the pulse frequency of the electrical stimulation to be delivered (192). The selected ramp schedule may be a ramp schedule that defines the amplitude ramp and the pulse width ramp for the concurrent ramping. Alternatively, processor 30 may select two different ramp schedules, one for amplitude and one for pulse width. In some examples, the pulse width ramp schedule may be based on the amplitude values of the amplitude ramp schedule. Once processor 30 selects the ramp schedule(s), processor 30 may begin to deliver electrical stimulation therapy at the starting amplitude and the starting pulse width of the ramp period defined by the selected ramp schedule (194).

If processor 30 determines that the ramp period is not complete ("NO" branch of block 196), processor 30 may increase the amplitude value according to the ramp schedule (198). Processor 30 may also decrease the pulse width according to the pulse width ramp schedule (200). Processor 30 may then deliver electrical stimulation with the increased amplitude value and decreased pulse width value (194). As described herein, although each pulse may have the amplitude value and pulse width value changed from the previous pulse, amplitude and pulse width changes may alternate between pulses or otherwise not occur for each pulse.

If processor 30 determines that the ramp period is complete ("YES" branch of block 196), processor 30 may continue stimulation with the current amplitude value and the current pulse width (202). If processor 30 does not receive a command to stop stimulation ("NO" branch of block 204), processor 30 may continue to deliver electrical stimulation (202). In response to receiving a command to stop stimulation ("YES" branch of block 204), processor 30 may stop delivery of the electrical stimulation therapy (206). Processor 30 may again deliver stimulation upon receiving a command (190).

Figure 12:
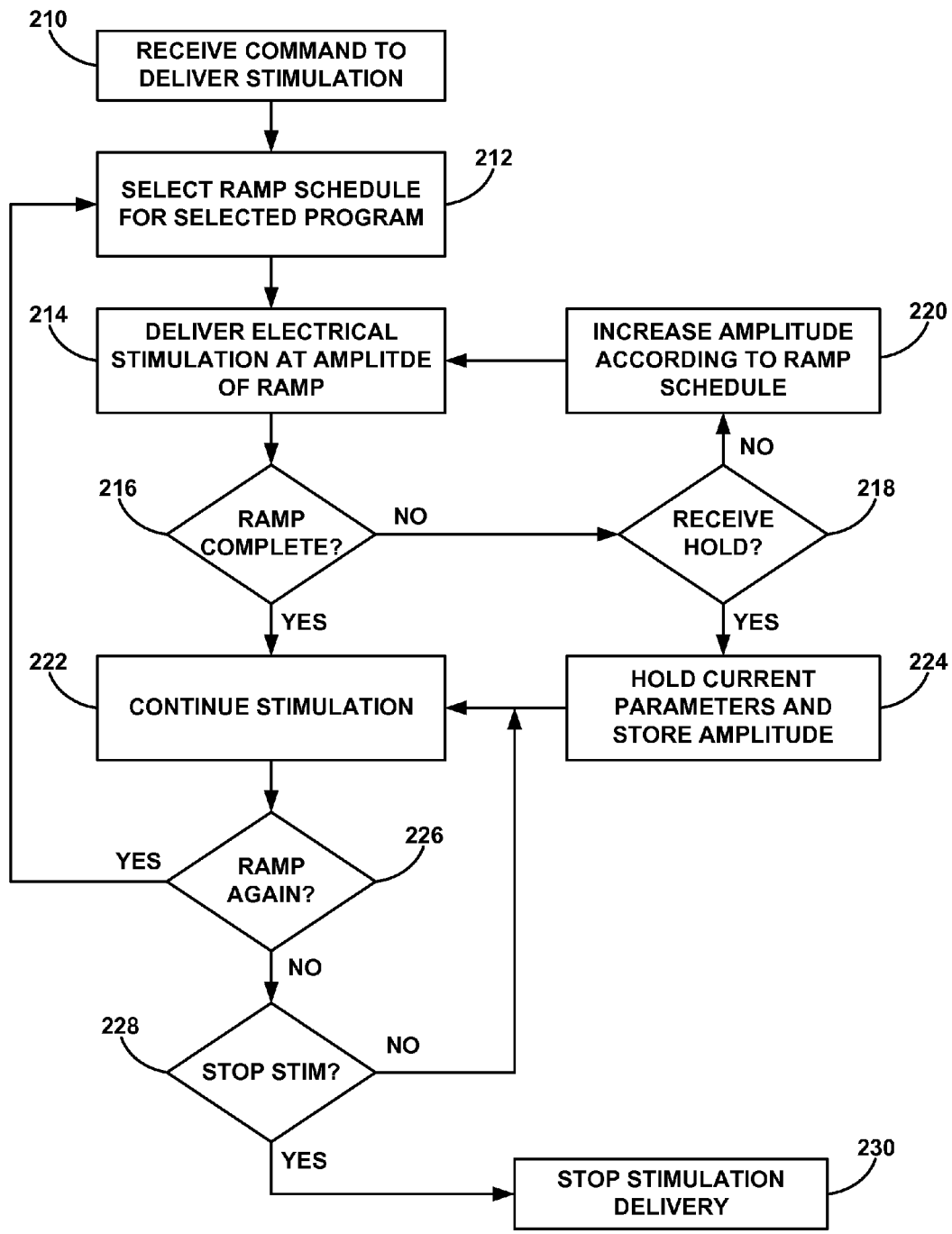
FIGS. 12 and 13 are flow diagrams that illustrate example processes for iteratively ramping an amplitude of electrical stimulation.
Figure 13:
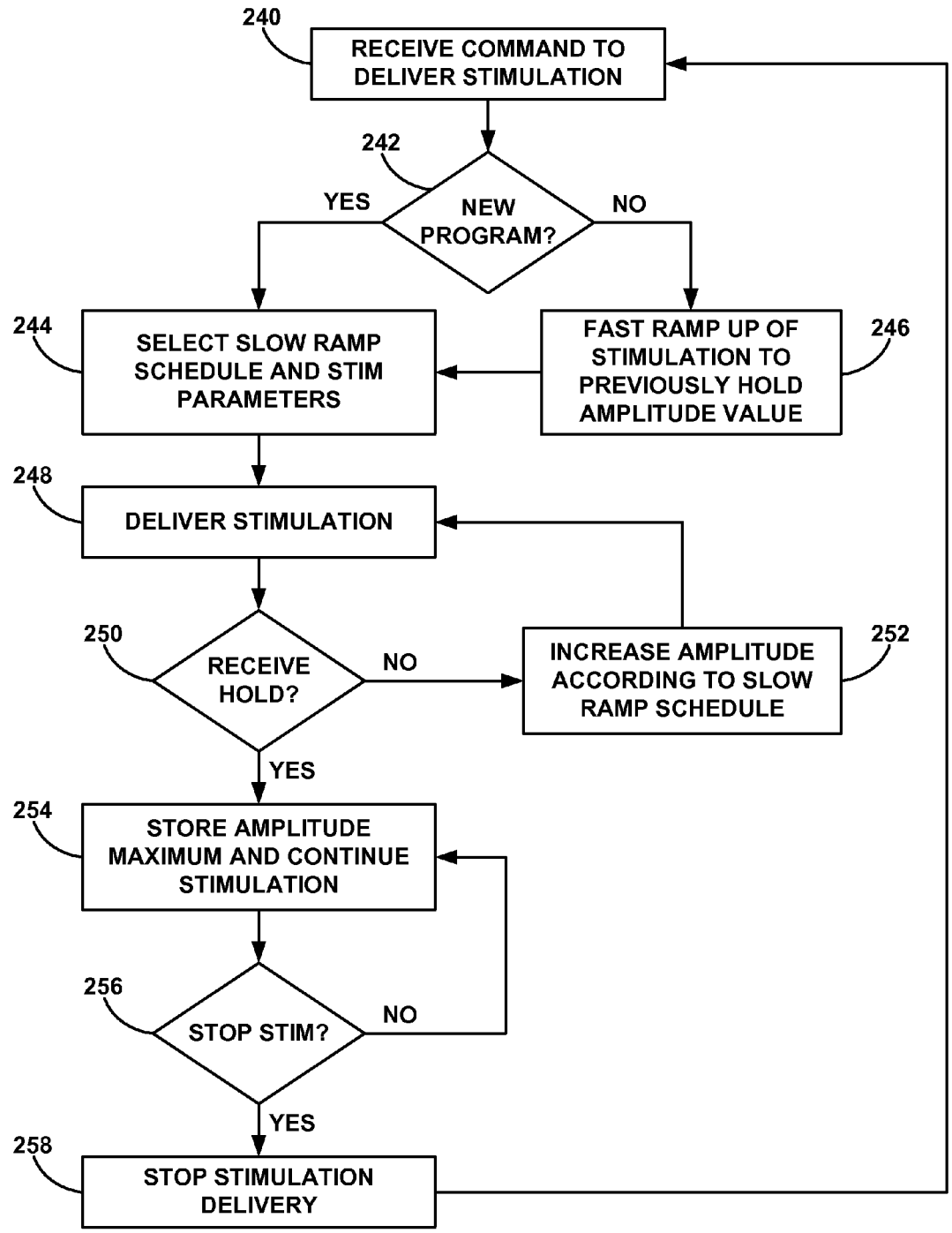

FIGS. 12 and 13 are flow diagrams that illustrate example processes for iteratively ramping an amplitude of electrical stimulation. Although processor 30 of IMD 14 will be described as generally performing the techniques of FIGS. 12 and 13, the techniques of FIGS. 12 and 13 may instead be performed by a combination of processors 30 and 50 of programmer 20 in other examples. FIG. 12 illustrates an example iterative ramping process with continuous stimulation. FIG. 13 illustrates an example iterative ramping process with non-continuous stimulation.

As shown in FIG. 12, processor 30 may receive a command to deliver electrical stimulation to patient 14 (210). The command may be in the form of an input to programmer 20 that is transmitted to IMD 14 or an automated command based on a detected signal or time from instructions stored in memory 30. Processor 30 may then select a ramp schedule for the selected program (212). Once processor 30 selects the ramp schedule, processor 30 may begin to deliver electrical stimulation therapy at the starting amplitude of the ramp period defined by the selected ramp schedule (214).

If processor 30 determines that the ramp period is not complete ("NO" branch of block 216), processor 30 may check to determine if a hold input has been received (218). If processor 30 has not received a hold input ("NO" branch of block 218), processor 30 may increase the amplitude value according to the ramp schedule (220). Processor 30 may then deliver electrical stimulation with the increased amplitude value (214). If processor 30 has received a hold input ("YES" branch of block 218), processor 30 may hold the current amplitude, for example, and store the amplitude as the hold amplitude value (224). Processor 30 may then continue stimulation with the hold amplitude value (222).

If processor 30 determines that the ramp period is complete ("YES" branch of block 216), processor 30 may continue stimulation with the current amplitude value and the other parameter values (222). If processor 30 determines that the amplitude should be ramped up again, due to a scheduled ramp or user input, for example ("YES" branch of block 226), processor 30 may again select the appropriate ramp schedule for further increasing of the amplitude from the hold amplitude value (214). If processor 30 is not to ramp amplitude again ("NO" branch of block 226), processor 30 may determine if stimulation is to be terminated, i.e., stopped (228). If processor 30 does not receive a command to stop stimulation ("NO" branch of block 228), processor 30 may continue to deliver electrical stimulation (222). In response to receiving a command to stop stimulation ("YES" branch of block 228), processor 30 may stop delivery of the electrical stimulation therapy (230).

In contrast to the iterative ramping process of FIG. 12, FIG. 13 illustrates an example iterative ramping process where amplitude is ramped upon returning to a previously used therapy program (e.g., a previously used parameter set). As shown in FIG. 13, processor 30 may receive a command to deliver electrical stimulation to patient 14 (240). The command may be in the form of an input to programmer 20 that is transmitted to IMD 14 or an automated command based on a detected signal or time from instructions stored in memory 30.

Processor 30 then determines if the electrical stimulation is defined by a new therapy program or a therapy program that has been previously used when iteratively ramping amplitude (242). If the program is not new ("NO" branch of block 242), processor 30 may select a fast ramp schedule that defines a fast ramp up of amplitude to the previously stored hold amplitude value (246). The hold amplitude value may be the maximum amplitude value reached during the previous ramp period. Once the fast ramp of amplitude has reached the hold amplitude value (246), processor 30 may select a slow ramp schedule and other stimulation parameters for slowing increasing the amplitude of stimulation (244).

If the program is a new program for iterative ramping ("YES" branch of block 242), processor 30 may select a slow ramp schedule and other stimulation parameters for slowly increasing the amplitude of stimulation (244). The slow ramp schedule may define a ramp period and/or a rate of increasing the amplitude to gradually increase the amplitude, and resulting stimulation intensity, to a tolerable and efficacious level for patient 12. Once processor 30 selects the ramp schedule, processor 30 may begin to deliver electrical stimulation therapy at the starting amplitude of the ramp period defined by the selected ramp schedule (248).

If processor 30 has not received a hold input ("NO" branch of block 250), processor 30 may increase the amplitude value according to the slow ramp schedule (252). Processor 30 may then deliver electrical stimulation with the increased amplitude value (248). If processor 30 has received a hold input ("YES" branch of block 250), processor 30 may hold the current amplitude, for example, store the amplitude as the hold amplitude value, and continue delivering stimulation with the hold amplitude value (254).

If processor 30 does not receive a command to stop stimulation ("NO" branch of block 256), processor 30 may continue to deliver electrical stimulation (254). In response to receiving a command to stop stimulation ("YES" branch of block 256), processor 30 may stop delivery of the electrical stimulation therapy (258). Processor 30 may then wait to receive a subsequent command to deliver stimulation therapy (240).

Figure 14A:
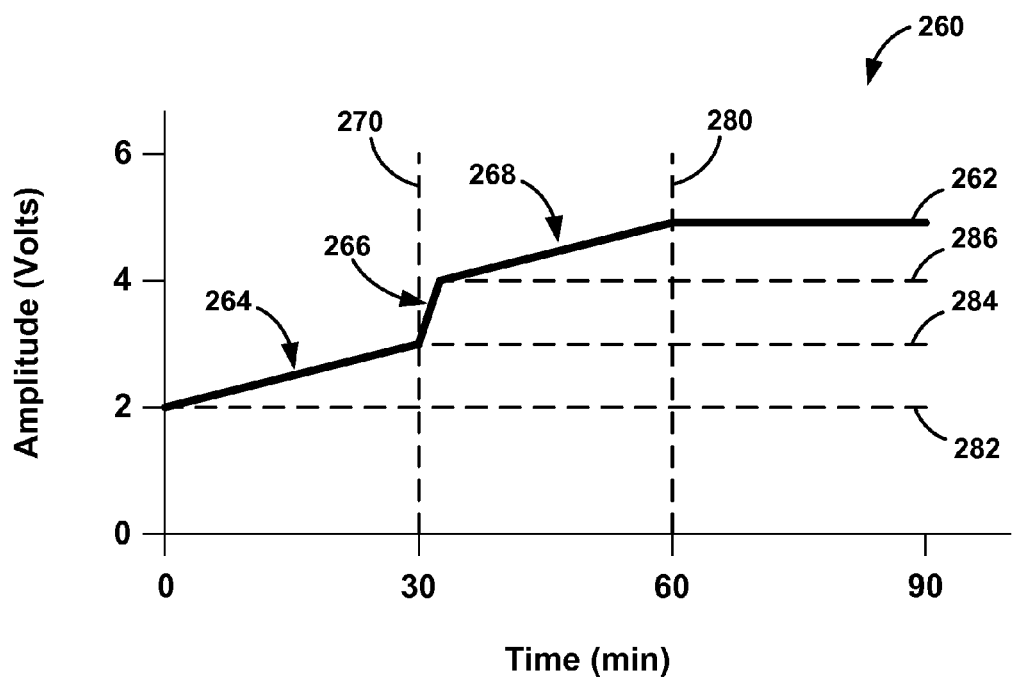
FIGS. 14A and 14B are graphs of example ramping techniques to adjust stimulation amplitude in response to a change in a patient posture state.
Figure 14B:
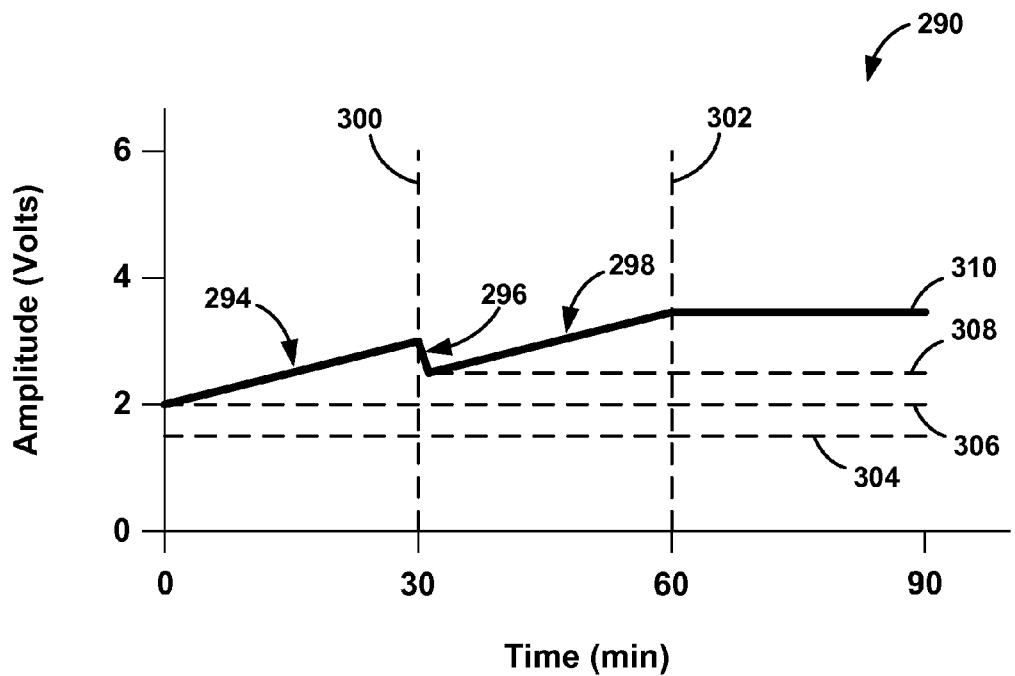

FIGS. 14A and 14B are graphs of example ramping techniques to adjust stimulation amplitude in response to a change in a patient posture state. The ramping techniques of FIGS. 14A and 14B may be used in conjunction with any ramping techniques described herein, such as those of FIGS. 8A, 8B, 9A, 9B, 12 and 13. FIGS. 14A and 14B generally describe techniques for modifying the amplitude value, or another parameter value, when a posture state change has been detected during a ramp period. In other words, in response to detecting a change in patient posture state, IMD 14 may interrupt a slow ramp period to quickly ramp to a new amplitude based on the new posture state. IMD 14 may subsequently resume the slow ramp period at the new amplitude.

As shown in FIG. 14A, graph 260 indicates an example change in amplitude during a slow ramp in amplitude and a change in posture state of patient 12. During daily activities, patient 12 may change posture, change activity, or otherwise move. A posture state may refer to a specific posture or activity assumed by patient 12. For example, IMD 14 may use one or more accelerometers to identify changes in the posture of patient 12. In this manner, IMD 14 may determine when patient 12 transitions between from one posture state to a different posture state (e.g., from lying down to standing up).

IMD 14 may begin to slowly ramp up amplitude as described herein. IMD 14 and/or processor 20 may select a ramp schedule for ramping over time (e.g., iterative ramping) and begin the ramp in amplitude. Ramp schedule 264 may define the increase in amplitude during the first ramp period between 0 minutes and 30 minutes. Ramp schedule 264 may be referred to as a slow ramp (e.g., a ramp schedule selected to increase the maximum amplitude tolerable by the patient) in some examples. The first posture state during ramp schedule 264 may be associated with baseline amplitude 282. Baseline amplitude 282 may be a value that was determined at the beginning of therapy (e.g., a perception threshold for each posture state), a therapeutic threshold, or even the most recent amplitude for the particular posture state when ramp schedule 264 began. Since patient 12 may benefit from different amplitudes for each posture state, the amplitude, or other parameters, may change for each posture state. A slow ramp in amplitude may need to be adjusted if a posture state change occurs during the slow ramp because different amplitudes may be used for different posture states.

At posture state change 270, IMD 14 may detect a change in the posture state of patient 12. For example, the posture state change may be patient 12 moving from a lying down posture state to a standing up posture state. In response to detecting the posture state change, IMD 14 may use a fast ramp to adjust amplitude 262 for the new posture state. The first posture state may have baseline amplitude 282 of approximately 2.0 volts. The second posture state may have baseline amplitude 284 of approximately 3.0 volts. Since amplitude 262 had increased approximately 1.0 volts from baseline amplitude 282 by the 30 minute mark, IMD 14 may increase amplitude 262 by 1.0 volts over baseline amplitude 284 of the second posture state by the end of ramp schedule 266. In other words, ramp schedule 266 may quickly increase amplitude 262 to the adjusted amplitude 286 as compensation for the change in posture state. Baseline amplitudes 282 and 284 may be stored in a memory (e.g., memory 32 of IMD 14).

Ramp schedule 266 may specify a certain increase rate or ramp period for achieving the new adjusted amplitude 286. The ramp period of ramp schedule 266 may be between approximately five seconds and five minutes. Ramp schedule 266 may alternatively or additionally specify a maximum increase rate that is tolerable by patient 12. In some examples, ramp schedule 266 may be based on the increase rate or ramp period of ramp schedule 264. For example, ramp schedule 266 may specify a fast ramp that is between two times faster and 20 times faster than the slow ramp of ramp schedule 264. After the fast ramp of ramp schedule 266 is complete, IMD 14 may resume the slow ramp of ramp schedule 268. Ramp schedule 268 may be defined by the same ramp rate, for example, as ramp schedule 264.

Interrupting a slow ramp with a fast ramp may be performed in response to any number of posture state changes during the slow ramp. The slow ramp of ramp schedule 264, for example, may thus continue across all posture states. In some examples, IMD 14 may increase the amplitude values for each posture state according to the slow ramp, whether patient 12 is engaged in the posture state or not. In other words, a slow ramp may be applied to the amplitudes stored in memory as a part of parameter sets for each posture state. In response to detecting a change in posture state, IMD 14 may use a fast ramp to adjust the amplitude to that of the parameters stored for the new posture state. Such a ramp may involve an increase or a decrease to the amplitude associated with the new posture state. Alternatively, IMD 14 may update the amplitude of a new posture state only in response to detecting the new posture state.

Hold input 280 may be received by programmer 20 and IMD 14 at approximately the 60 minute time point. In response to receiving hold input 280, IMD 14 may maintain the electrical stimulation at the amplitude of approximately 5.0 volts for a period of time. The period of time may be a predetermined period of time after hold input 280 is received or equal to the duration of which the user depresses or provides hold input 280. Alternatively, the period of time may be an open-ended period that continues until IMD 14 receives a request from patient 12 to change stimulation parameters or terminate stimulation or until IMD 14 changes a stimulation parameter value in response to a detected physiological change in patient 12 or other received instruction.

As shown in FIG. 14B, graph 290 indicates an example change in amplitude during a slow ramp in amplitude and a change in posture state of patient 12. Graph 290 may be similar to graph 260 of FIG. 14A; however, graph 290 provides a decrease to amplitude when the new posture state uses a lower amplitude value. In other words, patient 12 may be more sensitive to therapy in the new posture state and require a lower amplitude value for electrical stimulation to be efficacious. In this manner, IMD 14 may determine when patient 12 transitions from one posture state to a different posture state (e.g., from a standing up posture state to a sitting posture state).

IMD 14 may begin to slowly ramp up amplitude as described above. IMD 14 and/or processor 20 may select a ramp schedule for ramping over time (e.g., iterative ramping) and begin the ramp in amplitude. Ramp schedule 294 may define the increase in amplitude during the first ramp period between 0 minutes and 30 minutes. Ramp schedule 294 may be referred to as a slow ramp (e.g., a ramp schedule selected to increase the maximum amplitude tolerable by the patient) in some examples. The first posture state during ramp schedule 294 may be associated with baseline amplitude 306. Baseline amplitude 306 may be a value that was determined at the beginning of therapy (e.g., a perception threshold for each posture state), a therapeutic threshold, or even the most recent amplitude for the particular posture state when ramp schedule 294 began. Since patient 12 may benefit from different amplitudes for each posture state, the amplitude, or other parameters, may change for each posture state. A slow ramp in amplitude may need to be adjusted if a posture state occurs during the slow ramp because different amplitudes may be used for different posture states.

At posture state change 300, IMD 14 may detect a change in the posture state of patient 12. For example, the posture state change may be patient 12 moving from a standing up posture state to a sitting posture state or a lying down posture state. In response to detecting the posture state change, IMD 14 may use a fast ramp to adjust amplitude 310 for the new posture state. The first posture state may have baseline amplitude 306 of approximately 2.0 volts. The second posture state may have baseline amplitude 304 of approximately 1.6 volts. Since amplitude 310 had increased approximately 1.0 volts from baseline amplitude 306 by the 30 minute mark, IMD 14 may decrease amplitude 310 by 1.0 volts over baseline amplitude 304 of the second posture state by the end of ramp schedule 296. In other words, ramp schedule 296 may quickly decrease amplitude 310 to the adjusted amplitude 308 as compensation for the change in posture state. Baseline amplitudes 304 and 306 may be stored in a memory (e.g., memory 32 of IMD 14). In some examples, a fast decreasing ramp schedule may have a higher rate of decrease or shorter ramp period of a similar increasing ramp schedule. In other examples, ramp schedule 296 may even define a substantially immediate drop off (e.g., a ramp period of approximately zero seconds) in amplitude to adjusted amplitude 308.

After the fast ramp of ramp schedule 296 is complete, IMD 14 may resume the slow ramp of ramp schedule 298. Ramp schedule 298 may be defined by the same ramp rate, for example, as ramp schedule 294. Interrupting a slow ramp with a fast ramp may be performed in response to any number of posture state changes during the slow ramp. The slow ramp of ramp schedule 294, for example, may thus continue across all posture states, as described above.

Hold input 302 may be received by programmer 20 and IMD 14 at approximately the 60 minute time point. In response to receiving hold input 302, IMD 14 may maintain the electrical stimulation at the amplitude of approximately 3.5 volts for a period of time. The period of time may be a predetermined period of time after hold input 302 is received or equal to the duration of which the user depresses or provides hold input 302. Alternatively, the period of time may be an open-ended period that continues until IMD 14 receives a request from patient 12 to change stimulation parameters or terminate stimulation or until IMD 14 changes a stimulation parameter value in response to a detected physiological change in patient 12 or other received instruction.

Figure 15:
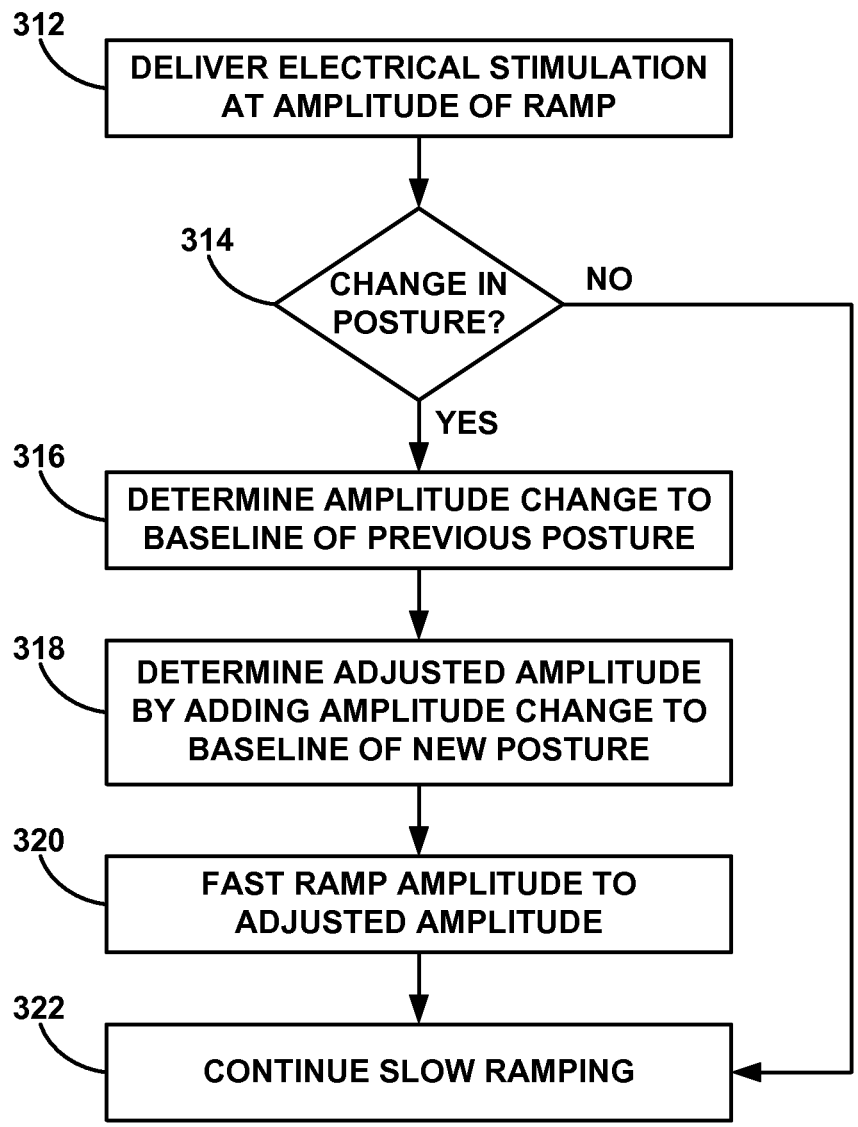
FIG. 15 is a flow diagram that illustrates an example process for adjusting an amplitude in response to changes in patient posture states.

FIG. 15 is a flow diagram that illustrates an example process for adjusting an amplitude in response to changes in patient posture states. Although processor 30 of IMD 14 will be described as generally performing the techniques of FIGS. 12 and 13, the techniques of FIGS. 12 and 13 may instead be performed by a combination of processors 30 and 50 of programmer 20 in other examples. The process of FIG. 15 may be utilized within the processes of FIG. 12 or 13. For example, the process of FIG. 15 may be implemented between blocks 214 and 216 of FIG. 12 or between blocks 248 and 250 of FIG. 13.

Processor 30 may deliver electrical stimulation at an amplitude of a selected ramp schedule (312). If processor 30 does not detect a change in posture state ("NO" branch of block 314), processor may continue the slow ramp (322). If processor 30 does detect a change in posture state ("YES" branch of block 314), processor 30 may determine the amplitude change that has occurred over the baseline amplitude of the previous posture state (316). In other words, processor 30 may identify the magnitude of which the amplitude value has changed with respect to the baseline amplitude of the previous posture state.

Processor 30 may then determine the adjusted amplitude needed for the new posture state (318). Processor 30 may calculate the adjusted amplitude by adding the amplitude change to the baseline amplitude of the new posture state. Processor 30 may then fast ramp the amplitude to the value of the adjusted amplitude for the new postures state (320). The adjusted amplitude is thus the target amplitude for the end of the fast ramp period. As described above, the fast ramp may be significantly faster than the slow ramp in order to effectively deliver therapy specific to the new posture state. Once the fast ramp is complete, processor 30 may continue the slow ramping of the amplitude during the new posture state (322). The process of FIG. 15 may be repeated for any number of changes to the posture state of patient 12 during a slow ramp process.

According to the techniques and devices described herein, one or more parameters may be ramped up or down to achieve efficacious stimulation therapy. For example, a ramp schedule that defines a ramp period may be selected based on a pulse frequency of the electrical stimulation. The ramp period may be longer for higher frequencies to allow the patient to tolerate the higher frequency electrical stimulation. In another example, pulse width may be ramped down as amplitude is ramped up. This concurrent ramping may allow the paresthesia area to remain relatively constant when increasing or decreasing stimulation intensity to the affected nerves. In an alternative example, an IMD may provide iterative ramping over time to gradually push or guide the patient into tolerating higher stimulation intensities that may provide more effective treatment of the patient's symptoms. Although ramping up (e.g., increasing the value of amplitude over time) is described herein, these techniques may similarly be used to ramp a parameter value down over time.

The disclosure also contemplates computer-readable storage media comprising instructions to cause a processor to perform any of the functions and techniques described herein. The computer-readable storage media may take the form of any volatile, non-volatile, magnetic, optical, or electrical media, such as a RAM, ROM, NVRAM, EEPROM, flash memory, or any other digital media. The computer-readable storage media may be non-transitory. A programmer, such as patient programmer or clinician programmer, may also contain a more portable removable memory type to enable easy data transfer or offline data analysis.

The techniques described in this disclosure, including those attributed to IMD 14, programmer 20, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 30 of IMD 14, processor 50 of programmer 20, or any one or more parts of the techniques described herein may be implemented by a processor of one of IMD 14, programmer 20, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

Various examples have been described. These and other examples are within the scope of the following claims.

The invention claimed is:

1. A method for controlling electrical stimulation therapy, the method comprising:
    obtaining, by one or more processors, a stimulation parameter set that at least partially defines an electrical stimulation signal deliverable to a patient, the stimulation parameter set comprising a signal frequency value of the electrical stimulation signal;
    selecting, by the one or more processors, an amplitude ramp schedule based on the signal frequency value of the stimulation parameter set; and
    increasing, by the one or more processors, an amplitude of the electrical stimulation signal during a ramp period defined by the amplitude ramp schedule.

2. The method of claim 1, wherein the ramp period defined by the ramp schedule is longer for higher signal frequency values than lower signal frequency values.

3. The method of claim 1, wherein:
    the ramp schedule defines a rate of increasing the amplitude; and
    the rate is lower for higher signal frequency values than lower signal frequency values.

4. The method of claim 1, further comprising delivering the electrical stimulation therapy to a patient when increasing the amplitude of the electrical stimulation signal.

5. The method of claim 1, further comprising:
    selecting, by the one or more processors, a pulse width ramp schedule based on the amplitude ramp schedule; and
    decreasing, by the one or more processors, a pulse width of the electrical stimulation signal while the amplitude is increased during the ramp period.

6. The method of claim 1, wherein the signal frequency value is a pulse frequency, and wherein the stimulation parameter set comprises the pulse frequency, an electrode configuration, a pulse width, and a target amplitude.

7. The method of claim 1, wherein:
    the stimulation parameter set comprises a starting amplitude;
    the starting amplitude is lower than a target amplitude; and
    the ramping schedule defines a rate of increasing the amplitude from the starting amplitude to the target amplitude.

8. The method of claim 1, wherein the signal frequency value is between approximately 1,000 Hz and 10,000 Hz.

9. The method of claim 1, wherein the ramp period is between approximately one minute and 8 hours.

10. The method of claim 1, wherein the one or more processors are housed within at least one of an implantable medical device and an external programmer.

11. A system comprising:
    a memory configured to store a plurality of amplitude ramp schedules; and
    at least one processor configured to obtain a stimulation parameter set that at least partially defines an electrical stimulation signal deliverable to a patient, the stimulation parameter set comprising a signal frequency value of the electrical stimulation signal, select one of the plurality of amplitude ramp schedules based on the signal frequency value of the stimulation parameter set, and increase an amplitude of the electrical stimulation signal during a ramp period defined by the selected amplitude ramp schedule.

12. The system of claim 11, wherein the ramp period defined by the ramp schedule is longer for higher signal frequency values than lower signal frequency values.

13. The system of claim 11, wherein:
the ramp schedule defines a rate of increasing the amplitude; and
the rate is lower for higher signal frequency values than lower signal frequency values.

14. The system of claim 11, further comprising a therapy module configured to deliver the electrical stimulation signal to a patient.

15. The system of claim 14, wherein the therapy module is configured to deliver the electrical stimulation signal to the patient when the at least one processor increases the amplitude of the electrical stimulation signal.

16. The system of claim 11, wherein the at least one processor is configured to select a pulse width ramp schedule based on the amplitude ramp schedule and decrease a pulse width of the electrical stimulation signal while the amplitude is increased during the ramp period.

17. The system of claim 11, wherein the signal frequency value is a pulse frequency, and wherein the stimulation parameter set comprises the pulse frequency, an electrode configuration, a pulse width, and a target amplitude.

18. The system of claim 11, wherein:
the stimulation parameter set comprises a starting amplitude;
the starting amplitude is lower than a target amplitude; and
the ramping schedule defines a rate of increasing the amplitude from the starting amplitude to the target amplitude.

19. The system of claim 11, wherein:
the signal frequency value is between approximately 1,000 Hz and 10,000 Hz; and
the ramp period is between approximately one minute and 8 hours.

20. The system of claim 11, further comprising an implantable medical device comprising at least one of the memory and the at least one processor.

21. The system of claim 11, further comprising an external programmer comprising at least one of the memory and the at least one processor.

22. An implantable medical device comprising:
a memory configured to store a plurality of amplitude ramp schedules; and
at least one processor configured to obtain a stimulation parameter set that at least partially defines an electrical stimulation signal deliverable to a patient, the stimulation parameter set comprising a signal frequency value of the electrical stimulation signal, select one of the plurality of amplitude ramp schedules based on the signal frequency value of the stimulation parameter set, and increase an amplitude of the electrical stimulation signal during a ramp period defined by the selected amplitude ramp schedule.

23. A computer-readable storage medium comprising instructions that cause at least one processor to:
obtain a stimulation parameter set that at least partially defines an electrical stimulation signal deliverable to a patient, the stimulation parameter set comprising a signal frequency value of the electrical stimulation signal;
select an amplitude ramp schedule based on the signal frequency value of the stimulation parameter set; and
increase an amplitude of the electrical stimulation signal during a ramp period defined by the selected amplitude ramp schedule.

* * * * *